US009713692B2

(12) United States Patent
Pujol et al.

(10) Patent No.: US 9,713,692 B2
(45) Date of Patent: Jul. 25, 2017

(54) HUMIDIFIER WITH BACK-FLOW PREVENTION VALVE

(71) Applicant: RIC INVESTMENTS, LLC, Wilmington, DE (US)

(72) Inventors: John Raymond Pujol, Murrysville, PA (US); Patrick Truitt, Mars, PA (US); Daniel R. Martin, Delmont, PA (US); Winslow Kevin Duff, Export, PA (US); Steven Adam Kimmel, Delmont, PA (US); Jeffrey Kepler, Export, PA (US); Peter Chi Fai Ho, Pittsburgh, PA (US); Lance Ranard Busch, Trafford, PA (US); Jerome Matula, Jr., Monroeville, PA (US); Drew A. Demangone, Latrobe, PA (US); Anthony J. Bafile, Windber, PA (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 0 days.

(21) Appl. No.: 14/658,307

(22) Filed: Mar. 16, 2015

(65) Prior Publication Data
US 2015/0182721 A1 Jul. 2, 2015

Related U.S. Application Data

(60) Division of application No. 11/713,990, filed on Mar. 5, 2007, now Pat. No. 8,997,740, which is a
(Continued)

(51) Int. Cl.
*A61M 16/16* (2006.01)
*A61M 16/20* (2006.01)
(Continued)

(52) U.S. Cl.
CPC .......... *A61M 16/16* (2013.01); *A61M 16/109* (2014.02); *A61M 16/162* (2013.01);
(Continued)

(58) Field of Classification Search
CPC ...... F16K 17/366; F16K 31/18; A61M 16/10; A61M 16/1045; A61M 16/1075–16/168
See application file for complete search history.

(56) References Cited

U.S. PATENT DOCUMENTS 3,155,746 A 11/1964 Banks
3,780,985 A 12/1973 Perry
(Continued)

FOREIGN PATENT DOCUMENTS

GB 2192136 A 1/1988
JP 2003245354 A 9/2003
(Continued)

*Primary Examiner* — Rachel Young
(74) *Attorney, Agent, or Firm* — Michael W. Haas

(57) ABSTRACT

A humidifier for use with a pressure support system. The humidifier includes a body having an inlet, a fluid holding chamber, and an outlet. The inlet is positioned upstream and in fluid communication with the fluid holding chamber. The outlet is positioned downstream of and in fluid communication with the fluid holding chamber. A back-flow preventing valve is positioned upstream of the fluid chamber. The back-flow preventing valve is movable between an open position, in which the inlet is unblocked, and a closed position in which the inlet is blocked. In the closed position, the back-flow preventing valve prevents fluid, fluid vapor, or both from entering the pressure support via the inlet to the humidifier.

11 Claims, 26 Drawing Sheets

Related U.S. Application Data continuation-in-part of application No. 11/527,052, filed on Sep. 26, 2006, now Pat. No. 8,701,662.

(60) Provisional application No. 60/720,763, filed on Sep. 27, 2005.

(51) Int. Cl.
*F24F 6/12* (2006.01)
*A61M 16/10* (2006.01)
*F24F 6/00* (2006.01)

(52) U.S. Cl.
CPC ............. *A61M 16/208* (2013.01); *F24F 6/12* (2013.01); *F24F 2006/008* (2013.01)

(56) References Cited

U.S. PATENT DOCUMENTS

| | | | |
|---|---|---|---|
| 3,864,440 A | 2/1975 | Giocoechea | |
| 4,054,622 A | 10/1977 | Lester | |
| 4,098,853 A | 7/1978 | Brown | |
| 4,269,213 A | 5/1981 | Sasaki | |
| 4,693,853 A | 9/1987 | Falb | |
| 4,739,898 A * | 4/1988 | Brown | A47J 31/4407 137/43 |
| 4,753,758 A | 6/1988 | Miller | |
| 4,825,860 A | 5/1989 | Falb | |
| 4,853,161 A | 8/1989 | Huang | |
| 5,421,110 A | 6/1995 | Morrissey | |
| 5,438,981 A | 8/1995 | Starr | |
| 5,462,100 A * | 10/1995 | Covert et al. | 141/59 |
| 5,647,355 A | 7/1997 | Starr | |
| 5,664,563 A | 9/1997 | Schroeder | |
| 5,865,171 A | 2/1999 | Cinquin | |
| 5,878,743 A | 3/1999 | Zdrojkowski | |
| 6,398,197 B1 | 6/2002 | Dickinson | |
| 6,435,180 B1 | 8/2002 | Hewson | |
| 6,772,999 B2 | 8/2004 | Lipscombe | |
| 6,923,181 B2 | 8/2005 | Tuck | |
| 6,935,844 B1 | 8/2005 | Dukes | |
| 7,066,174 B1 | 6/2006 | Smith | |
| 7,111,624 B2 | 9/2006 | Thudor | |
| 7,334,596 B1 | 2/2008 | Chesters | |
| 7,357,145 B2 | 4/2008 | Soderberg | |
| 7,484,531 B2 * | 2/2009 | Hoogenakker et al. | 137/879 |
| 2001/0050080 A1 | 12/2001 | Seakins | |
| 2003/0029316 A1 | 2/2003 | Campbell | |
| 2003/0066526 A1 | 4/2003 | Thudor | |
| 2004/0055597 A1 | 3/2004 | Virr | |
| 2004/0060559 A1 | 4/2004 | Virr | |
| 2006/0055069 A1 | 3/2006 | DiMatteo | |
| 2007/0102541 A1 | 5/2007 | MacLean-Blevins | |
| 2008/0072900 A1 | 3/2008 | Kenyon | |

FOREIGN PATENT DOCUMENTS

| | | |
|---|---|---|
| WO | WO02066106 A1 | 8/2002 |
| WO | WO02066107 A1 | 8/2002 |
| WO | WO2005018724 A1 | 3/2005 |

\* cited by examiner

HUMIDIFIER WITH BACK-FLOW PREVENTION VALVE

CROSS-REFERENCE TO RELATED APPLICATIONS

This application is a Divisional of U.S. patent application Ser. No. 11/713,990, filed 5 Mar. 2007, which is a continuation-in-part of U.S. patent application Ser. No. 11/527,052, which was filed 26 Sep. 2006, now U.S. Pat. No. 8,701,662, granted Apr. 22, 2014 and which claims priority under 35 U.S.C. §119(e) from provisional U.S. patent application No. 60/720,763, filed 27 Sep. 2005, the contents of each of which are incorporated herein by reference.

BACKGROUND OF THE INVENTION

1. Field of the Invention

The present invention relates to a humidifier and, more particularly, to a humidifier used in a pressure support system that includes a valve to prevent a back-flow of fluid from the humidifier into a pressure support device.

2. Description of the Prior Art

There are numerous situations where it is necessary or desirable to deliver a flow of breathing gas to the airway of a patient. For example, it is known to ventilate a patient using a technique known as non-invasive ventilation. It is also known to deliver continuous positive airway pressure (CPAP) or variable airway pressure, which varies with the patient's respiratory cycle or a monitored condition of the patient, to treat a medical disorder, such as sleep apnea syndrome, in particular, obstructive sleep apnea (OSA), or congestive heart failure. Non-invasive ventilation and pressure support therapies involve the placement of a patient interface device, which is typically a nasal or nasal/oral mask, on the face of patient to interface the ventilator or pressure support device with the airway of the patient so that a flow of breathing gas can be delivered from the pressure/flow generating device to the airway of the patient.

It is also desirable in many instances in both invasive and non-invasive ventilation to humidify the flow of gas provided to the patient. To this end, humidification systems have been developed that include a humidification chamber provided in-series with a pressure support device to add moisture to the gas output by the pressure support device. FIG. 1 illustrates an example of a conventional configuration in which a pressure support device 10 having an outlet port 12 supplies pressurized gas to a patient circuit 13, which is an elongated flexible tube. Patient circuit 13 is connected to an inlet port 14 of a humidifier 16. Humidifier 16 includes a humidification chamber 15 that is filled with fluid, typically water or distilled water. An outlet port 18 of humidifier chamber 15 is coupled via patient circuit 20 to a patient interface (not shown), such as a nasal mask. In operation, pressurized gas from pressure support device 10 passes through patient circuit 13 to humidifier 16. The gas interacts with the water in the humidifier chamber and exits into tubing 20 where it is communicated to an airway of a patient. Some conventional humidification systems include a heater operatively coupled to humidifier chamber 15 to facilitate the humidification process.

One reason patient circuit 13 is provided between the humidification chamber and pressure support device 10 is to prevent fluid from flowing from the humidifier back into the pressure support device should the humidifier 16 be tipped over. Water entering pressure support device 10 could damage the device.

It is also known to couple the outlet of pressure support device 10 directly to the inlet of the humidification chamber, as shown, for example, in FIG. 2. In this configuration the humidification chamber is rigidly coupled to the pressure support device. However, this configuration exacerbates the problem of fluid flowing from the humidification chamber back into the pressure support device, because of the direct and close connection between the inlet port of the humidification chamber and the outlet port of the pressure support device.

An attempt to prevent back-flow of water from a humidification chamber in the pressure support device using a snorkel-like inlet to the humidification chamber is disclosed in U.S. Pat. No. 6,398,197. While the snorkel type of configuration taught by this patent may help minimize water from entering the outlet of the pressure support device due to backsplash or tilting of the system, it does not prevent water from entering the pressure support device due to condensation and rainout, i.e., water contained in the gas or vapor that may flow back from the humidification chamber into the pressure support device. In addition, in certain orientations at certain water levels, such as if the pressure support device and humidifier are tilted on their side and the humidification chamber even merely half full, the snorkel configuration of the '197 patent has little or no ability to prevent the back-flow of fluid from the humidification chamber into the pressure support device.

SUMMARY OF THE INVENTION

Accordingly, it is an object of the present invention to provide a humidifier for use in a pressure support system that overcomes the shortcomings of conventional humidification devices. This object is achieved according to one embodiment of the present invention by providing a humidifier that includes a body having an inlet adapted to be operatively coupled to an outlet of a pressure support device such that a flow of gas generated by such a pressure support device is communicated to the inlet. The humidifier also includes a fluid holding chamber and an outlet. The inlet is positioned upstream and in fluid communication with the fluid holding chamber, and the outlet is positioned downstream of and in fluid communication with the fluid holding chamber. A valve is positioned in the inlet and upstream of the fluid chamber. The valve is movable between an open position in which the inlet is substantially unblocked and a closed position in which the inlet is substantially blocked.

It is a further object of the present invention to provide a pressure support system that overcomes the shortcomings of conventional pressure support systems. This object is achieved by providing a pressure support system that includes a pressure support device, which is adapted to generate a flow of gas, and a humidifier. The humidifier has a body having an inlet, a fluid holding chamber, and an outlet. The inlet is positioned upstream and in fluid communication with the fluid holding chamber, and the outlet is positioned downstream of and in fluid communication with the fluid holding chamber. In addition, a first valve is positioned between an outlet of the pressure support device and the inlet of the humidifier. The first valve is movable between an open position, in which a gas flow path between the outlet of the pressure support device and the inlet of the humidifier is substantially unblocked, and a closed position, in which the gas flow path is substantially blocked. Movement between these positions is accomplished based on a first physical orientation of the pressure support system, for example whether it is tilted, whether it is sitting flat or level, or both.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise

DETAILED DESCRIPTION OF THE EXEMPLARY EMBODIMENTS

Figure 1:
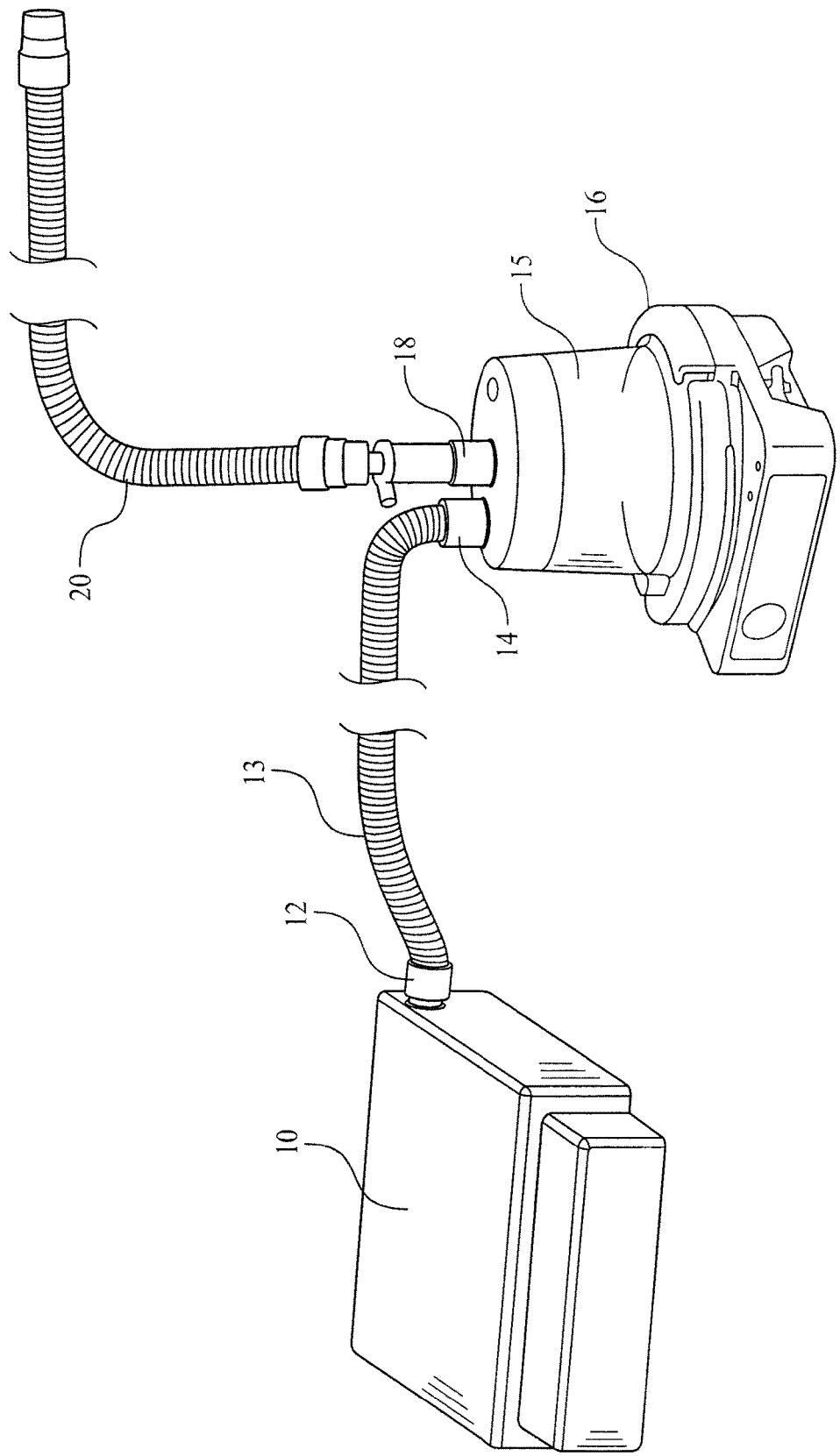
FIG. 1 is a top perspective view of a prior art stand alone humidifier coupled to a pressure support device.
Figure 2:
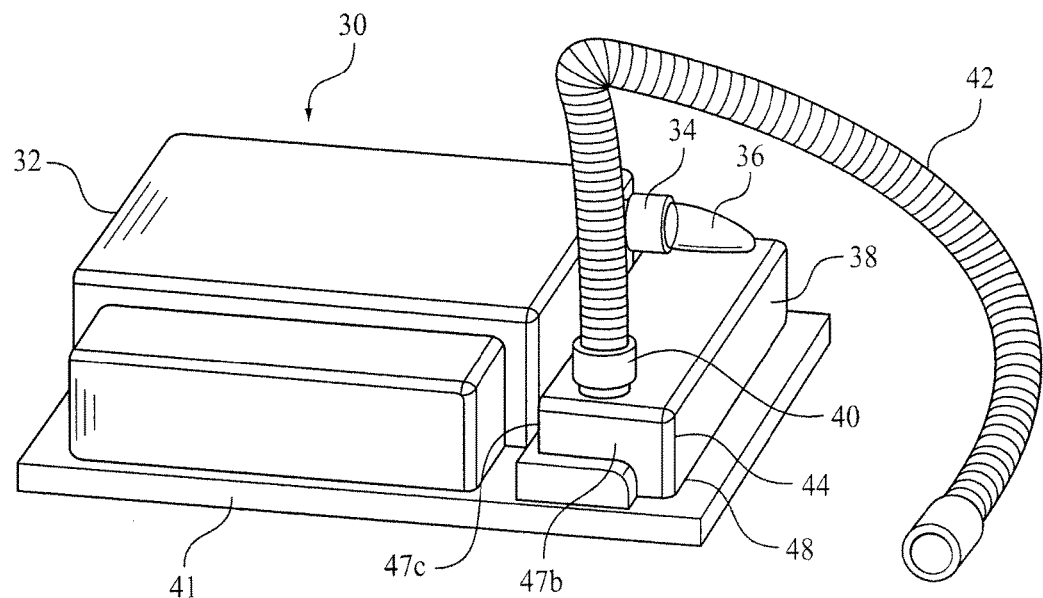
FIG. 2 is a top perspective view of a pressure support system including a humidifier and a pressure support device according to the principles of the present invention.
Figure 3:
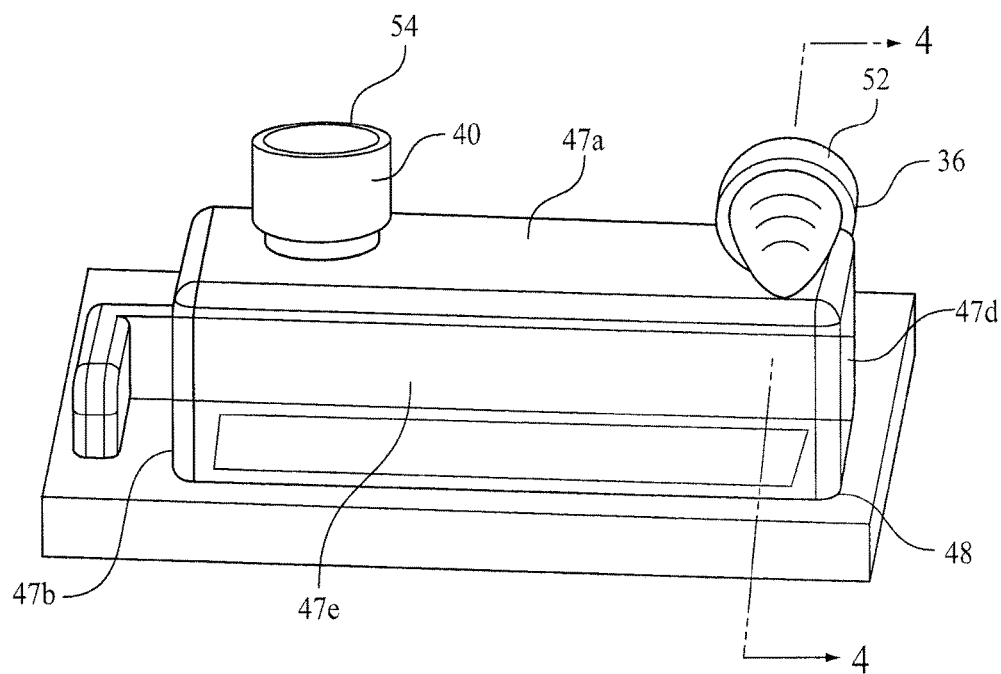
FIG. 3 is a front perspective view of the humidifier used in the system of FIG. 2.
Figure 4:
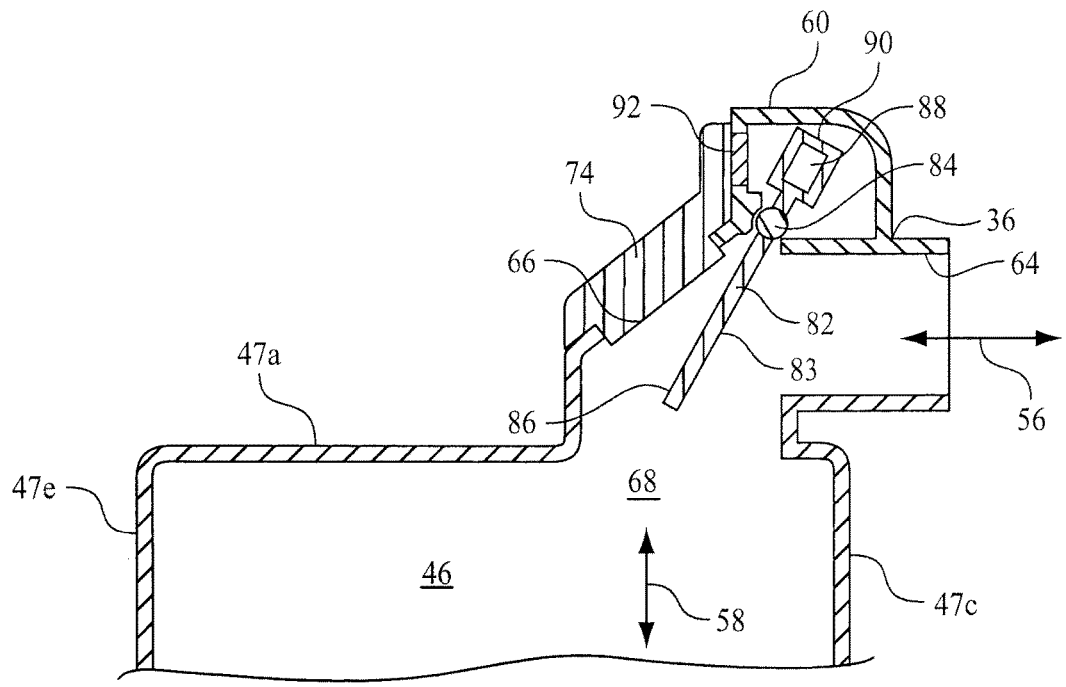
FIG. 4 is a sectional view of the humidifier shown in FIG. 3, taken along line 4-4 of FIG. 3, with a valve shown in a partially open position.

FIGS. 2-5 illustrate a pressure support system 30 that includes a pressure support device 32 and a humidifier 38 according to the principles of the present invention. Pressure support device 32 has an outlet port 34 fluidly coupled to an inlet port or inlet passageway 36 (referred to as an "inlet") of humidifier 38. Humidifier 38 also includes an outlet port or exit passageway 40 (referred to as an "outlet"), which is fluidly coupled to a patient circuit 42.

Pressure support device 32 is any conventional ventilation or pressure support device or system capable of generating a flow of gas for delivery to an airway of a patient. Examples of such pressure support systems include, but are not limited to: a ventilator, a continuous positive airway pressure (CPAP) device, or a variable pressure device, e.g. an auto-titrating device, proportional assist ventilation (PAV®) device, proportional positive airway pressure (PPAP®) device, C-Flex™ device, Bi-Flex® device, or a BiPAP® device manufactured and distributed by Respironics, Inc. of Murrysville, Pa., in which the pressure provided to the patient varies with the patient's respiratory cycle so that a higher pressure is delivered during inspiration than during expiration, or other pressure support device.

The present invention contemplates that a patient interface (not shown) is capable of being coupled to the distal end of patient circuit 42, i.e., the end distal from humidifier 38. The patient interface is any appliance, either invasive or non-invasive, such as a nasal mask, nasal/oral mask, total face mask, nasal cannula, endotracheal tube, or tracheal tube, suitable for communicating a supply of breathable gas to the airway of a patient. Patient interface assembly may include headgear for mounting the appliance on the head of a patient.

Humidifier 38 includes a body 44 defining a fluid holding chamber 46. In an exemplary embodiment of the present invention, the fluid holding chamber is formed from a polymeric material, such as a clear polycarbonate material. Fluid holding chamber 46 is defined by an upper surface 47*a* and sidewalls and 47*b* through 47*e*. The body 44 attaches to a substantially flat base 48. Inlet 36 and outlet 40 are defined on upper surface 47*a*, with the inlet being disposed on an upstream side 52 of humidifier 38 and outlet 40 being defined on a downstream side 54 of the humidifier. Inlet 36 is upstream and in fluid communication with fluid holding chamber 46, and outlet 40 is downstream and in fluid communication with the fluid holding chamber. The upstream end of inlet 36 is oriented in a horizontal direction, as indicated by arrow 56, and directs gas to a downwardly direction towards fluid holding chamber 46, and outlet 40 is oriented in a vertical upward direction, as indicated by arrow 58, from the fluid holding chamber 46.

In the illustrated exemplary embodiment, humidifier 38 and pressure support device 32 are co-located on a common base 41 so that the entire assembly is joined as a unit. It is to be understood that the present invention contemplates other techniques for joining or integrating the humidifier and the pressure support device, including coupling them together directly without the use of a base or providing the humidifier and the pressure support device as an integrated unit, e.g., unified in a common housing. It is to be further understood that the present invention contemplates that the humidifier and the pressure support device need not be located on a common base, but may be separable or permanently separated from one another. In the illustrated embodiment, the outlet of the pressure support device is proximate to and rigidly coupled to the inlet of the humidifier. The present invention also contemplates separating the humidifier and the pressure support device and coupling the outlet of one with the inlet of the other via a tubing, flexible or rigid. In addition, the present invention contemplates providing a heating element associated with the humidifier. For example, a conventional hot plate or the wire heater can be used in, on, or near the humidifier to heat the fluid contained therein.

A valve arrangement 60 is disposed within or positioned on inlet 36. Valve arrangement 60 is similar to that disclosed in U.S. Pat. Nos. 5,647,355 and 5,438,981, the contents of which are incorporated herein by reference. Valve arrangement 60 is provided within the inlet passageway and includes a primary inlet portion 64, i.e., the inlet that communicates with the flow of gas from the pressure support device, and an outlet portion 68. Inlet 36 also includes an exhaust vent 66 disposed so as to communicate the fluid holding chamber with an ambient atmosphere. In the illustrated exemplary embodiment, outlet portion 68 is oriented so as to direct a flow of gas entering the inlet toward fluid holding chamber 46. Exhaust vent 66 is open to ambient atmosphere and is protected from unintended blockage by means such as raised vanes 74, a grate, or the like.

Further, according to the present invention, valve arrangement 60 includes a self-regulating flap-like valve element 82 that controls gas flow through primary inlet portion 64 and exhaust vent 66, whereby the valve element regulates gas flow into humidifier 16. Valve element 82 is constructed and arranged such that it is responsive to either positive pressure produced by the gas flow of the pressure support device 32 or negative pressure produced by a user's inhalation.

Valve element 82 is formed of a generally planar and substantially rigid member 83 pivotably supported at an intermediate region thereof by outwardly and oppositely directed, linear pivot pins 84, which are journaled within bearing formations provided in inlet 36. Valve element 82 further includes a closure portion 86 of dimension sufficient to cover primary inlet portion 64 or exhaust vent 66 when positioned, respectfully, over one of these openings.

In this present exemplary embodiment, valve element 82 is constructed such that it is as nearly weight-balanced as possible with respect to the pivot axis formed by pivot pins 84. In an exemplary embodiment of the present invention, closure portion 86 is counter poised by a counterweight 88 of substantially the same weight as closure portion 86. As a consequence of counterweight 88, the coefficient of friction between the pivot pins 84 and their associated valve housing bearing formations, as well as the intrinsic inertia of the valve element 82, in the absence of any other forces, the valve element is disposed such that closure portion 86 covers primary inlet portion 64 and tends to remain in that position. The closure portion covers the primary inlet portion until acted upon by a displacement force. In which case, the valve element moves to cover the exhaust vent. As a result, during normal operation of the pressure support system, that displacement force is provided by the positive pressure associated with the flow of pressurized respiratory gas from pressure support device 32. Thus, when the pressure support device is operating normally, valve element 82 assumes a position in which exhaust vent 66 is closed and a substantially unobstructed path is provided through the inlet from the pressure support device into the humidification chamber so that gas flows from primary inlet portion into humidification chamber 46.

Should the pressurized gas flow be cut off or reduced below a threshold level for any reason, the user's inhalation following such gas flow reduction of cessation would exert a negative pressure on the underside of closure member 86, thereby causing valve element 82 to pivot outwardly and cover primary inlet portion 64. Because valve element 82 is upright biased to a closed position with the valve elements so disposed, the user would have complete access to ambient air through exhaust vent 66. Exhalation by the user will also tend to maintain valve element 82 in the closed position due to the positive pressure applied on the valve element. This situation will continue until such time that the pressure flow is restored, whereupon the positive pressure produced by the pressurized gas would again compel valve element 82 to pivot upwardly, thereby closure portion 86 would cover exhaust vent 66 and a flow of gas from the pressure support device to the patient via the humidifier would be resumed.

To minimize flutter of valve element 82 as a pivot between its first and second positions, counterweight 88 preferably includes a suitable motion damping arrangement, such as a small permanent magnet 90 affixed proximate a first end of the valve element 82. Magnet 90 is magnetically attracted to an element 92, such as a small metallic or magnetic strip 92, for example, a steel strip or magnet, affixed to the interior of inlet 36. As will be appreciated, the respective positions of magnet 90 and metallic strip 92 may be reversed, if desired.

Figure 5:
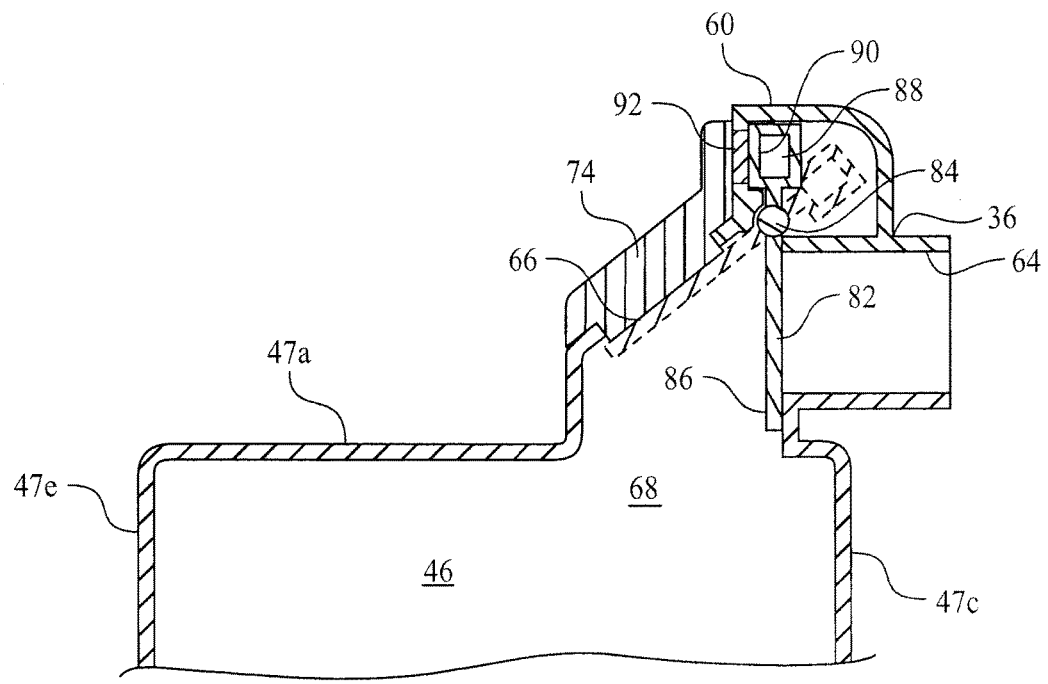
FIG. 5 is the same view as FIG. 4, with the valve in a fully closed position (the fully open position is shown in phantom)

The present invention also contemplates providing a bias force on valve element 82. This bias force can be applied to bias valve element 82 in the open position (unblocking primary inlet 64) or to bias the valve element in the closed position (blocking primary inlet 64, as shown in FIG. 5). Any conventional technique can be used to apply this bias force, including gravity (by weighting a portion of the valve element), springs, or magnets.

In operation, and referring to FIG. 5, humidifier 38 receives water or other fluid in fluid holding chamber 46. Typically, the fluid is provided to chamber 46 via outlet 40. More specifically, the user uncouples the patient circuit normally attached to the outlet and pours water or other fluid, fluid mixture, etc. into the fluid holding chamber. A pressure support device provides pressurized gas, such as air, from an outlet of the pressure support device to an inlet 36 of the humidifier. The pressurized gas causes valve element 82, as described above, to open, thereby blocking exhaust vent 66 and creating a flow passageway by opening primary inlet portion 64 permitting the flow of gas to be directed downwardly via the downstream side of the inlet and interact with the fluid contained within the fluid holding chamber. In other words, valve element 82 is in this open position (shown in phantom) only if there is a positive pressure at primary inlet portion 64, i.e., a pressure above that in chamber 46. Stated another way, there must be a pressure drop above an opening pressure value across valve element 82, as measured in the upstream direction to the downstream direction.

Humidified gas exits from outlet 40. The gas then travels through the patient circuit to the airway of the patient. Should the pressure provided by the pressure support device cease or fall below a threshold, valve element will become "free-floating", assuming the valve element is not biased. In which case, if the humidifier become knocked, jostled, or moved, the valve element can move to the closed position shown in FIG. 5 so that fluid is blocked from passing through inlet port 36 by blocking primary inlet portion 64. For example, fluid impacting on the valve element can cause it to move to the closed position. In addition, exhaust valve 66 will become unblocked. If the valve is biased to the closed position, the decrease in pressure will result in the valve automatically moving to the closed position. In this configuration, fluid is prevented from traveling into pressure support device 32. Once the fluid no long imparts a force on the valve element or the pressure provided by the pressure support device is restored to a level exceeding the force applied on the valve element by the fluid, if any, the valve element can move to open primary inlet port 64 and block exhaust vent 66. Should the pressure support device fail or fail to operate properly, then the patient can still breathe ambient air as described hereinabove, because valve element 82 will block primary inlet portion 64 and unblock exhaust vent 66.

Figure 6:
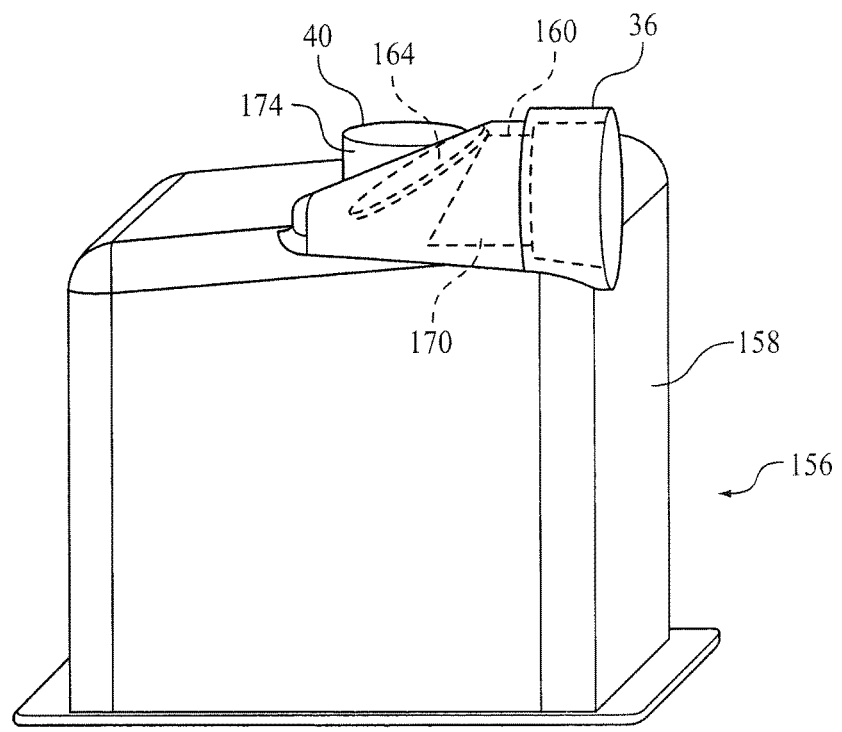
FIG. 6 is a side sectional view of a second embodiment of humidifier according to the principles of the present invention showing the valve in an open position.
Figure 7:
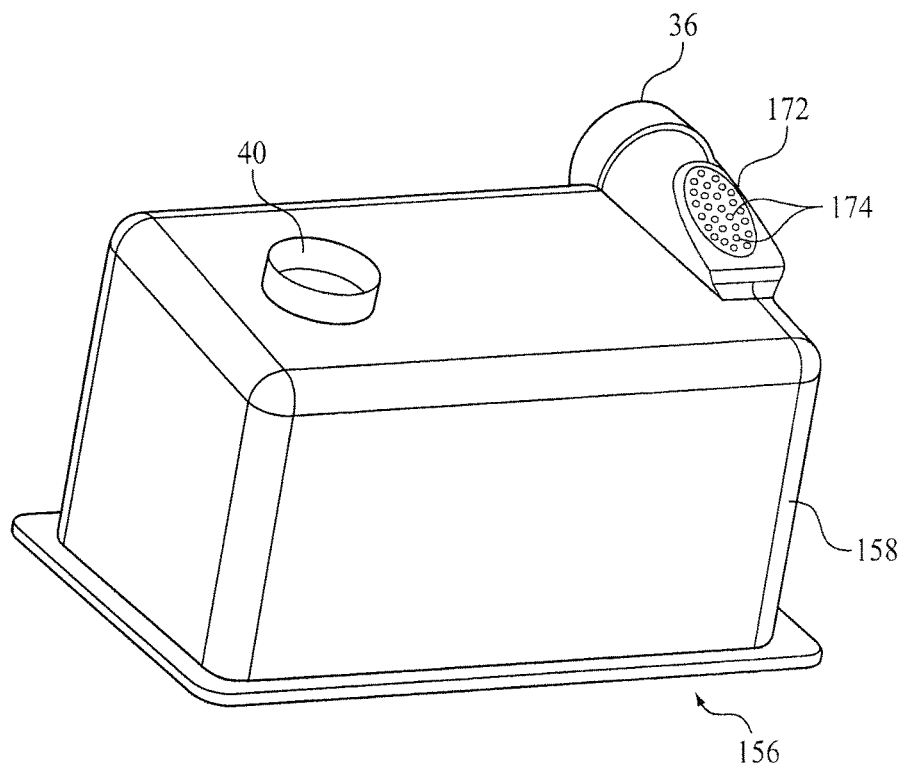
FIG. 7 is a front perspective exploded view of the humidifier shown in FIG. 6.
Figure 8:
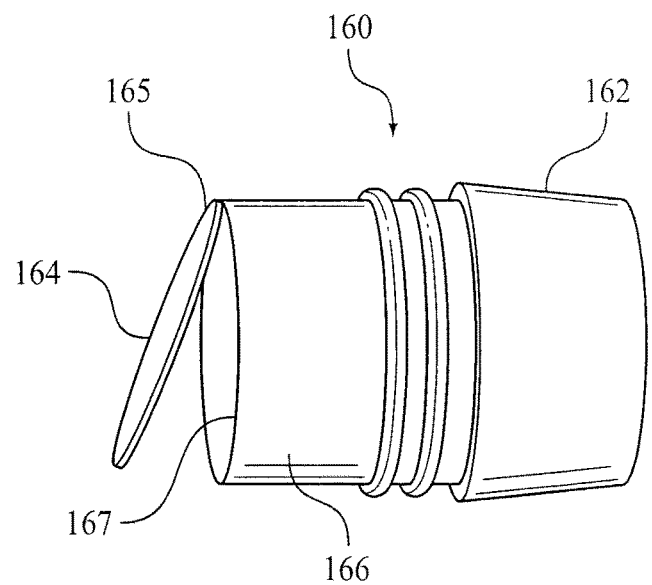
FIG. 8 is a side view of a valve used in the humidifier of FIG. 6.

FIGS. 6-8 show a second embodiment of humidifier 156 that includes a body 158 and a valve arrangement 160. Valve arrangement 160 includes a cylindrical member 162 having a flexible movable flap 164 attached thereto. In an exemplary embodiment, cylindrical member 162 is formed from a flexible material, such as silicone, rubber, or a combination thereof. Flap 164 is attached at one end 165 to cylindrical member 162 via a central portion 166. In an exemplary embodiment, cylindrical member 162, flap 164, and central portion 166 are formed form a unitary molded piece of material.

In an optional exemplary embodiment, a rigid overmolded ring or cylinder (not shown) is placed about a portion of the valve arrangement 160 to provide structure support for the valve. Valve 160 is adapted (sized and configured) to be positioned within inlet 36 of body 158. In a further optional embodiment, an exhaust vent 172 is positioned downstream of flap 164. Exhaust vent 172 includes a plurality of opening 174 to communicate gas from within the humidification chamber to the ambient atmosphere.

Operation of valve arrangement 160 is similar to that previously described for valve arrangement 60. However, flap 164 is biased so as to remain in a closed position, in which the flap substantially blocks an opening 167 defined in central portion 166 of the inlet. Pressurized gas coming from pressure support device entering inlet 36 causes the flap 164 to move outwardly, blocking exhaust vent 172 and unblocking the inlet to the humidifier. As a result, gas flows into the humidification chamber, where it is humidified by the fluid contained therein. The humidified gas exits the chamber via outlet 34, as previously described.

Should the flow of gas from the pressure support device drop below a predetermined pressure threshold, flap 164 will move to the closed position, thereby preventing any vapor or fluid carried by the gas contained in the humidifier from entering the pressure support device. When flap 164 is in the closed position, the patient breathes through the exhaust vent 172. It should be emphasized, however, that the exhaust vent is optional. If the humidifier is tipped, the weight of the water on flap 164 can cause the flap to move to the closed position, blocking opening 167, thereby preventing water from splashing or flowing back into the pressure support device via inlet 38.

Valve arrangement 160 is advantageous in that it can be retrofit onto an existing humidification chamber merely by inserting the valve arrangement into the inlet of the humidification chamber. Similarly, it is easily removable from the humidification chamber for cleaning and replacement purposes.

FIGS. 9-12 illustrate a third embodiment of a humidifier 256 that includes a body 258 and a valve arrangement 260 made in accordance with the principles of the present invention. This valve arrangement is similar to previously described valve arrangement 60. Valve arrangement 260 fits within inlet port 36. Specifically, valve arrangement 260 includes a cylindrically shaped overmolded arrangement 262 that receives a cylindrical ring 264. A valve element 266 is pivotably secured to the cylindrical ring 264 and/or overmolded arrangement 262. Valve element 266 includes a closure element or flap 268 and a counterweight blocking member or secondary flap 270 coupled thereto. Overmolded arrangement 262 includes an offset passageway that functions as an exhaust vent 272 to communicate a passage defined in cylindrical ring 264 and/or overmolded arrangement 262 with ambient atmosphere. An optional exhaust vent cover, such as a plurality of openings, can be positioned over exhaust vent 272. In an exemplary embodiment of the present invention, secondary flap 270 includes a magnet 276, and a metallic attraction member 278 is positioned in close proximity to the magnet, so that the magnet is attracted to member 278, causing secondary flap 270 to be biased in a closed position causing closure element 268 to block cylindrical ring 264.

Figure 10:
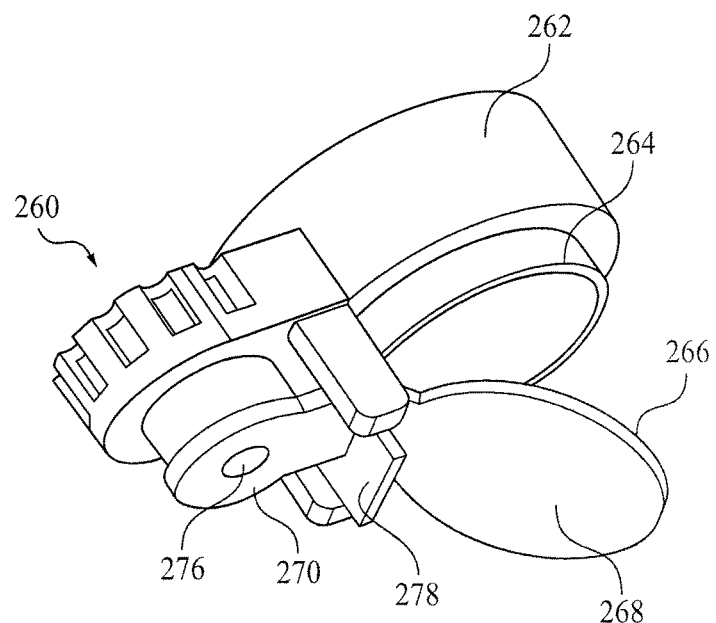
FIG. 10 is a front perspective view of a valve used in the humidifier of FIG. 9 shown in an open position.
Figure 11:
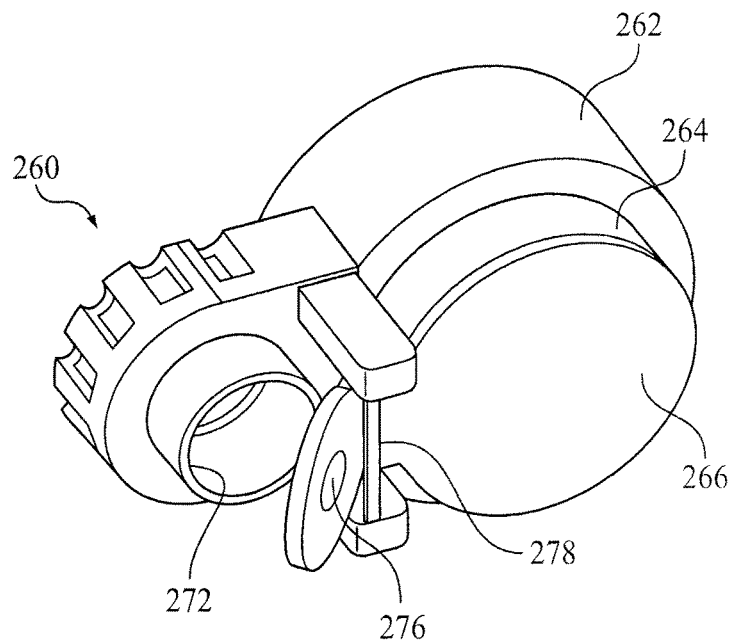
FIG. 11 is a front perspective view of the valve of FIG. 10 shown in a closed position.
Figure 12:
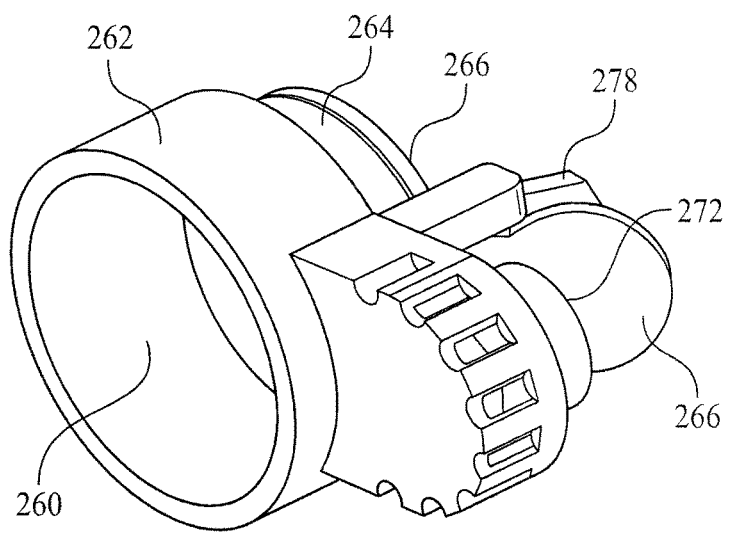
FIG. 12 is a rear perspective view of the valve of FIG. 10 shown in a closed position.

In operation, as shown in FIG. 10, pressurized gas from the pressure support device causes closure element 268 to overcome the biasing force provided by the magnet and substantially unblock cylindrical ring 264. Pressurized gas is then able to pass through inlet 36 into the humidification chamber defined by body 258 where it is humidified, and then exits via outlet 40. As shown in FIGS. 11 and 12, if the flow of gas from the pressure support device drops below a predetermined pressure threshold, valve element 266 will move to the closed position, thereby preventing any vapor or fluid carried by the gas contained in the humidifier from entering the pressure support device. When valve element 266 is in the closed position, the patient breathes through the exhaust vent 272. In addition, if fluid, such as water, is moved adjacent to inlet 36, closure element 268 can be biased by the weight of the fluid to the closed position. However, the patient can still breathe, because blocking member 270 is positioned away from exhaust vent 272 permitting the patient to breathe ambient air.

Figure 13:
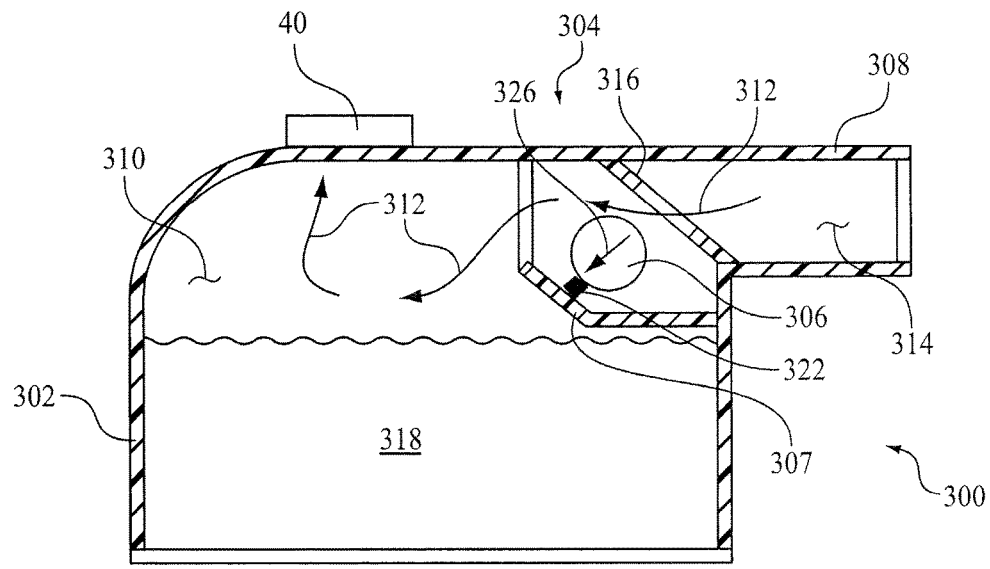
FIG. 13 is a side sectional view of a fourth embodiment of humidifier according to the principles of the present invention showing the valve in an open position.
Figure 14:
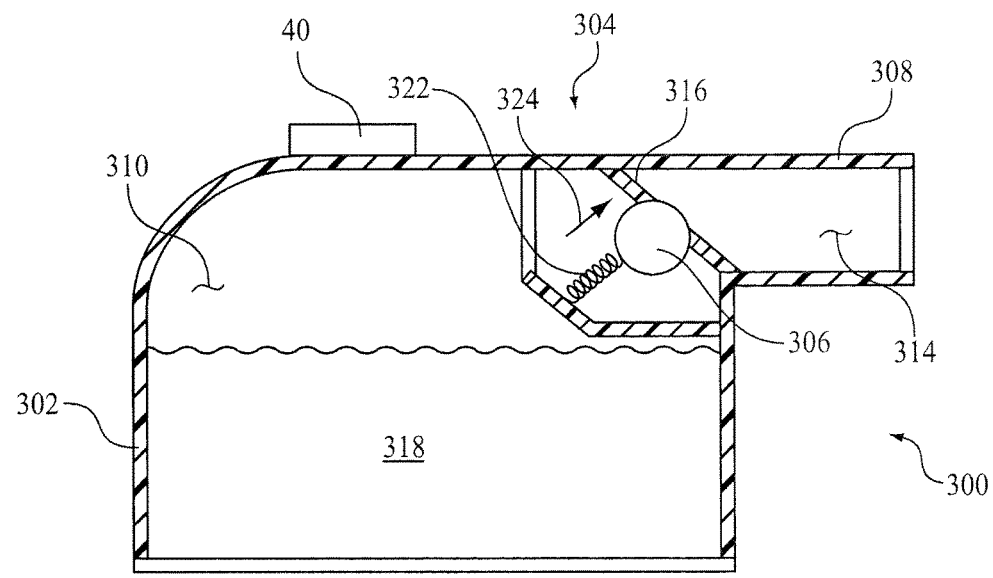
FIGS. 14 and 15 are side sectional views of the humidifier of FIG. 13 showing the valve in a closed position.
Figure 15:
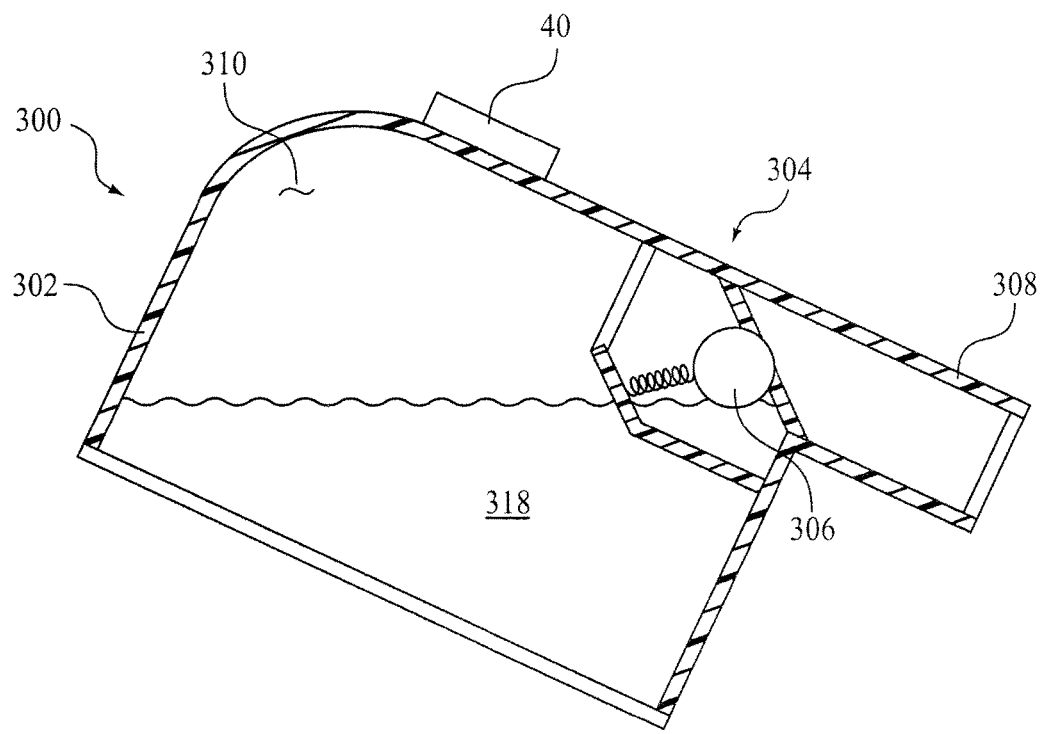

FIGS. 13-15 illustrate a third embodiment of a humidifier 300 that includes a body 302 and a valve arrangement, generally indicated at 304, made in accordance with the principles of the present invention. In this embodiment, valve arrangement 304 includes a floating element, in particular, a ball 306 that blocks and unblocks an inlet 308 of the humidifier. The ball is supported in or attached to body 302 by a support structure 307. Ball 306 is movable relative to body 302 between an open position, shown in FIG. 13 and a closed position, shown in FIGS. 14 and 15. In the open position, gas flows through the humidifier as indicated by arrows 312, i.e., through a passage 314 in inlet 308 and through cavity 310 and out outlet 40. In the closed position, ball 306 is seated on a seat 316, thereby blocking passageway 314 and, hence, preventing fluid or fluid laden vapor from flowing back into the pressure support device from the inlet. In an exemplary embodiment, support structure 307 is configured such that gas and liquids flow freely in or around the support structure. For example, the support structure can be a cage or a bracket with a plurality of openings.

In an exemplary embodiment, ball 306 has a density that is less than the water or fluid 318 contained within a fluid holding chamber 320 of humidifier 300 so that the ball will float on the fluid. As a result, if the height of a fluid 318 exceeds a certain level, which can occur if, for example, the humidification chamber is filled too full and/or is tilted so that the fluid flows toward the inlet, ball 306 will float on the fluid and block downstream end of inlet 306. This situation is illustrated in FIG. 15, which shows the humidifier tilted so that that water level is not longer horizontal, but is tilted toward inlet 306.

In the illustrated embodiment, ball 306 is biased to the closed position by a biasing mechanism, which is a compressed spring 322. Spring 322 is also oriented so as to assist the closure of seat 316 by ball 306 in the event that the ball floats to the closed position. That is, the spring serves as a guide to keep the ball oriented as it floats on the fluid so that it will properly engage seat 316. The biasing force applied on ball 306 by spring 322, which is indicated by arrow 324, is such that it can be overcome by the normal flow of gas from the pressure support device into the humidifier. That is, when the pressure support system is operating normally, ball 306 is moved to the open position, as indicated by arrow 326, by a pressure sufficient to overcome the spring bias. Thus, a substantially unobstructed flow of gas 312 is provided through the humidifier during normal operation of the pressure support system.

If, however, the pressure of the flow of gas falls below the bias force applied on ball, the spring will cause this ball to rest on seat 316, thereby, blocking inlet 308, as shown in FIG. 14. This is desirable, because a flow of gas having such as small or no pressure would likely allow some of the humidifier gas from the humidifier to flow back into the pressure support device by flowing via inlet 308. Ball 306, when seated on seat 316, prevents or minimizes the flow of gas back out of the inlet so that humidifier gas does not enter the outlet of the pressure support device. The presence of humidifier gas in the pressure support device is also undesirable because it could result in an accumulation of a significant amount of fluid in the pressure support device over time due to condensation, and may promote bacteria growth.

Although the floating element that blocks the inlet is illustrated as being a ball, it can be appreciated that other configurations, geometrical shapes, and differently sized elements may be provided. Similarly, the biasing mechanism is illustrated as being a spring. However, other biasing devices, such as a magnet, leaf spring, or other devices may be employed to bias the valve in the closed position.

Figure 16:
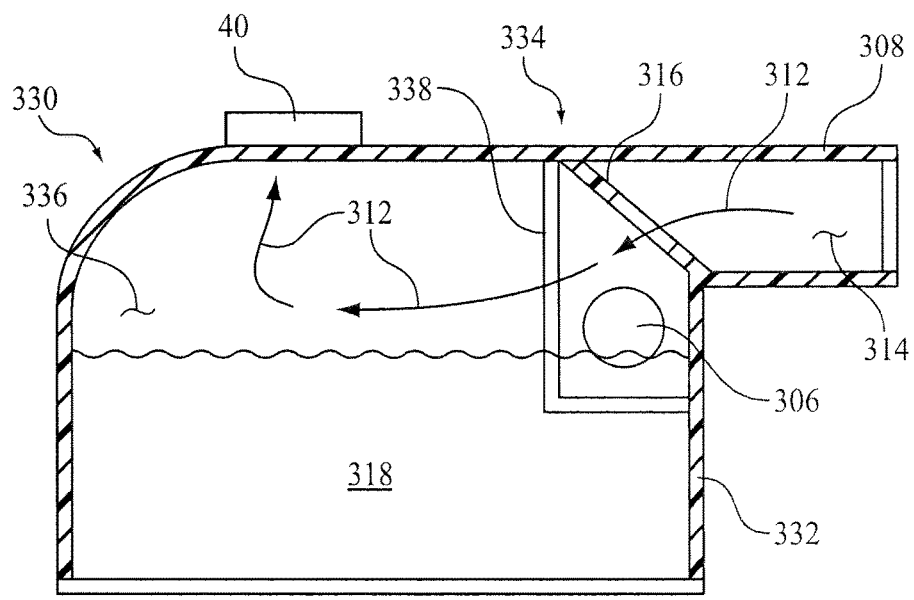
FIG. 16 is a side sectional view of a fifth embodiment of a humidifier according to the principles of the present invention showing the valve in an open position.
Figure 17:
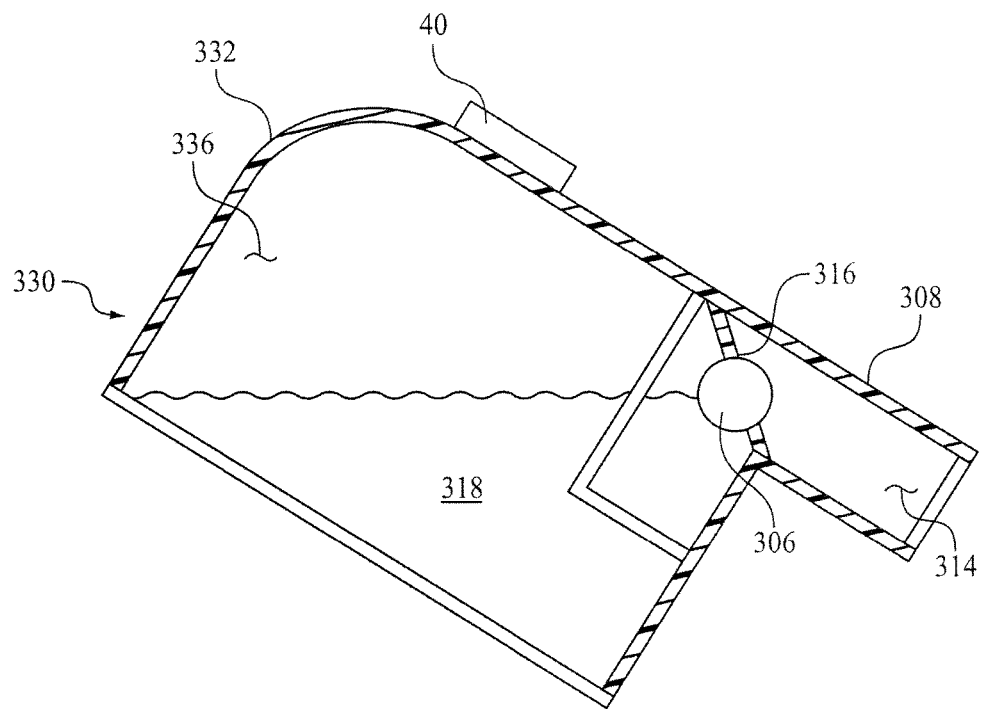
FIG. 17 is a side sectional view of the humidifier of FIG. 16 showing the valve in a closed position.

FIGS. 16 and 17 illustrated a fifth embodiment of a humidifier 330 having a body 332 and a valve arrangement, generally indicated at 334, according to the principles of the present invention. This embodiment is generally similar to the previous embodiment in that it uses a float valve, i.e., a ball 306, to selectively block and unblock a valve seat 316. The level of fluid 318 in a fluid holding chamber 336 of body 332 causes ball 306 to rise and fall within a support structure 338. Support structure 338, like support structure 307, guides the ball into the valve seat as the fluid rises or shifts in the fluid holding chamber. Preferably, support structure 338 allows gas and liquid to flow freely to ball 306.

During normal operation, as shown in FIG. 16, the level of fluid 318 is such that the ball is spaced apart from valve seat 316 and a substantially unobstructed gas flow path is provided at the inlet of the humidifier to the fluid holding chamber. Thus, gas flows relatively freely into the fluid holding chamber as indicated by arrows 312. As the humidifier tilts, as shown in FIG. 17, or the fluid level otherwise rises, the fluid pushes ball 306 into seat 316, thereby blocking passageway 314 and preventing fluid and gas from flowing back out of inlet 308. Thus, the level of fluid 318 controls the blocking and unblocking of inlet 318.

Unlike the previous embodiment, humidifier 330 does not include a biasing mechanism for urging the valve to a closed position based on the pressure of the flow of gas delivered to inlet 308. Thus, this embodiment does not block the inlet of the humidifier based on the operation of the pressure support device. However, it still accomplishes the function of preventing or minimizing the backsplash or back-flow of fluid out of the inlet of the humidifier.

Figure 18:
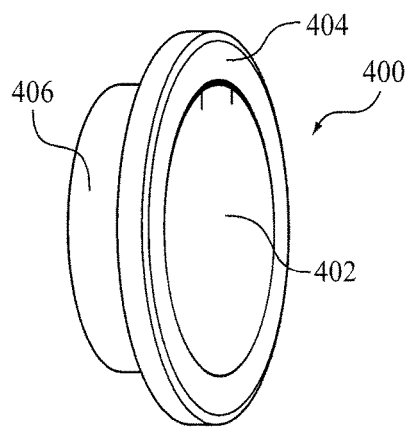
FIG. 18 is a perspective view of a sixth embodiment of a valve suitable for use in a humidifier according to the principles of the present invention showing the valve in a closed position.
Figure 19:
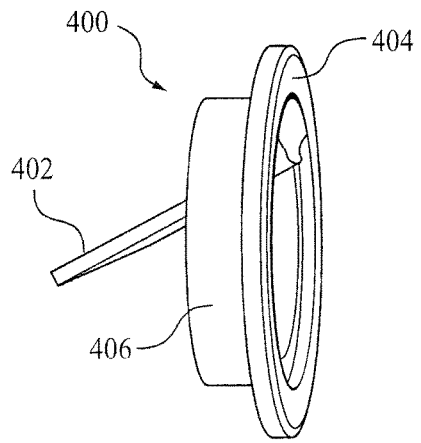
FIG. 19 is a perspective view of the valve of FIG. 18 showing the valve in an open position.

Yet another embodiment for a valve arrangement 400 suitable for use in a humidifier according to the principles of the present invention is shown in FIGS. 18 and 19. Valve 400 simply inserts into the inlet of the humidifiers. Thus, it is easily retrofit unto most conventional humidifier. Valve arrangement 400 includes a flexible flapper 402 attached to a cylindrical ring 404 and operates similarly to valve arrangement 160. A flange 406 is provided for securing the valve to the inlet of the humidifier. Flapper 402 is biased in a closed position (FIG. 18).

In operation, pressurized air from pressure support device 32 causes flapper 402 to open and permit the pressurized air to pass through the inlet and become humidified by the fluid contained within the humidifier. If fluid is splashed toward the valve arrangement 400 or the pressurized air ceases to flow from the pressure support device, then flapper 402 closes over ring 404, thereby preventing fluid from flowing upstream from the inlet of the humidifier into the pressure support device.

Figure 20:
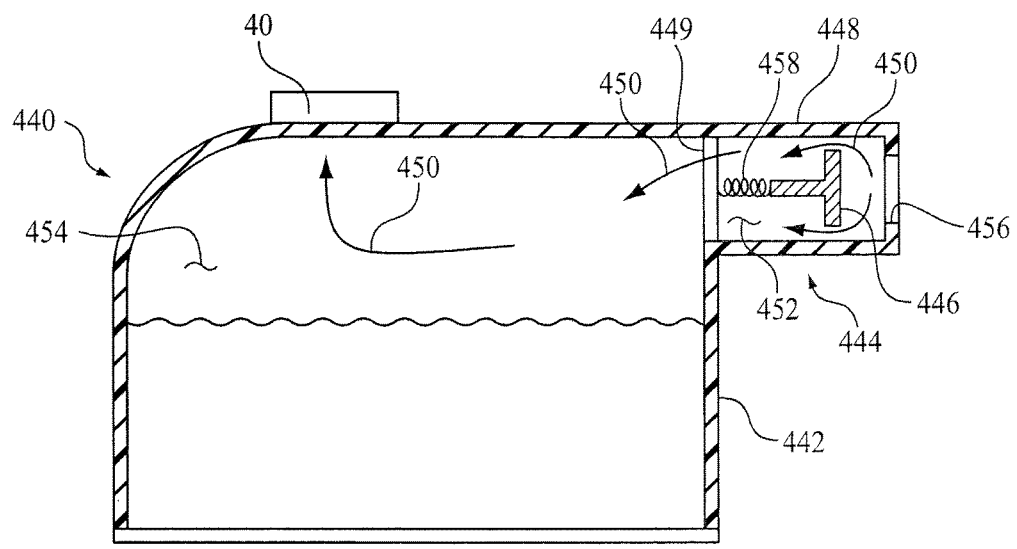
FIG. 20 is a side sectional view of a seventh embodiment of a humidifier according to the principles of the present invention showing the valve in an open position.
Figure 21:
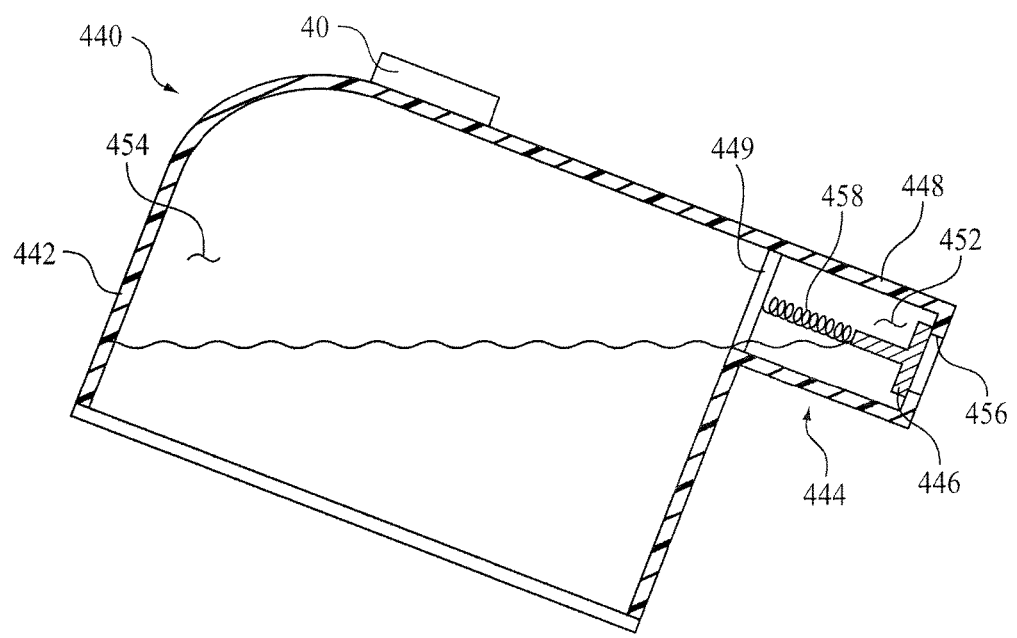
FIG. 21 is a side sectional view of the humidifier of FIG. 20 showing the valve in a closed position.

FIGS. 20 and 21 illustrate a seventh embodiment of a humidifier 440 that includes a body 442 and a valve arrangement, generally indicated at 444, according to the principles of the present invention. In this embodiment, valve arrangement 444 includes a valve member 446 that blocks and unblocks an inlet 448 of the humidifier. The valve member is supported in or attached to body 442 by a support structure 449. Valve member 446 is movable relative to body 442 between an open position, shown in FIG. 20 and a closed position, shown in FIG. 21. In the open position, gas flows through the humidifier as indicated by arrows 450, i.e., through a passage 452 in inlet 448 and through cavity 454 and out outlet 40. In the closed position, valve member 446 is situated so as to seal an opening 456 provided in inlet 448, thereby blocking passageway 452 and, hence, preventing fluid or fluid laden vapor from flowing back into the pressure support device from the inlet. In an exemplary embodiment, valve member 446 is configured such that gas and liquids flow freely in or around the valve member yet seals opening 456 when in the closed position.

In the illustrated embodiment, valve member 446 is biased to the closed position by a biasing mechanism, which is a compressed spring 458. Spring 458 is also oriented so as to assist the closure of opening 456 by valve member 446. That is, the spring serves as a guide to keep the valve member oriented so that it will properly seal opening 456. Of course, other mechanisms can be provided for ensuring that the valve member is properly seated over the opening of the inlet. The biasing force applied on valve member 446 by spring 458 is such that it can be overcome by the normal flow of gas from the pressure support device into the humidifier. That is, when the pressure support system is operating normally, valve member 446 is moved to the open position by a pressure sufficient to overcome the spring bias. Thus, a substantially unobstructed flow of gas 450 is provided through the humidifier during normal operation of the pressure support system.

If, however, the pressure of the flow of gas falls below the bias force applied on valve member, the spring will cause valve member 446 to close or seal opening 456, thereby, blocking inlet 448, as shown in FIG. 21. This is desirable for the reasons discussed above.

It can be appreciated that the valve element that blocks the inlet can have a variety of configurations, geometrical shapes, and sizes so long at the functions of sealing the inlet during closure and allowing a flow of gas when open are accomplished. For example, one embodiment of the present invention contemplates that opening 456 is circular and valve element 446 is a disk having a stem extending therefrom to which the spring is attached. Similarly, the biasing mechanism, which is illustrated as being a spring, can have other configurations, such as a magnet, leaf spring.

Figure 22:
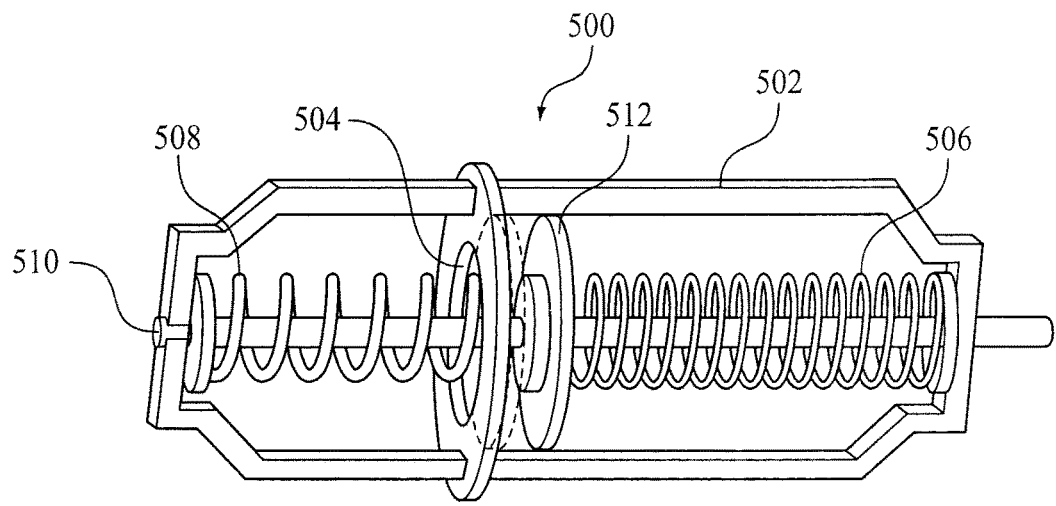
FIG. 22 is a perspective view of an eighth embodiment of a valve suitable for use in a humidifier according to the principles of the present invention.
Figure 9:
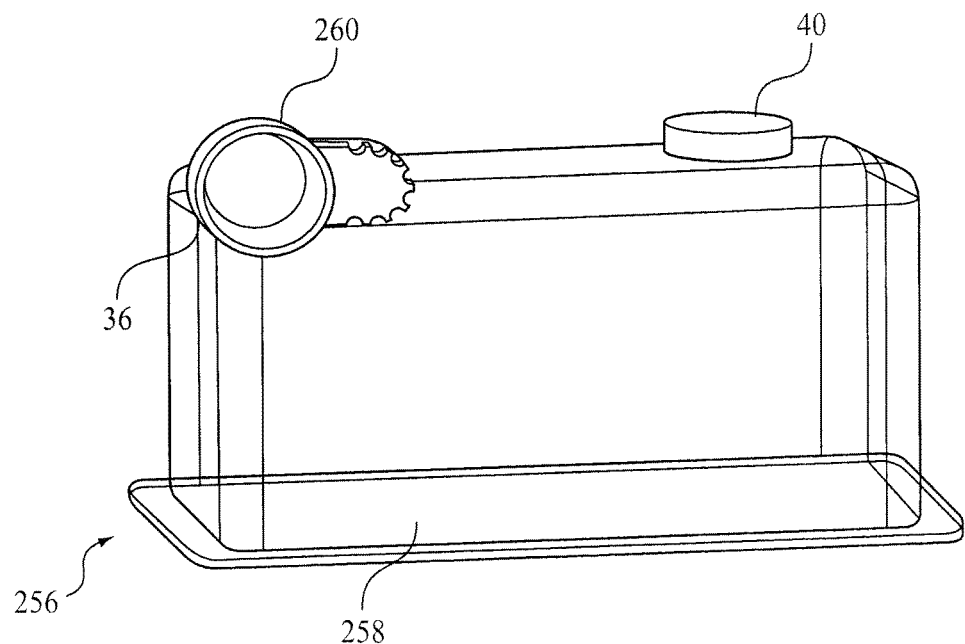
FIG. 9 is a rear perspective view of a third embodiment of humidifier according to the principles of the present invention.

FIG. 22 shows a valve arrangement 500 that may be used in addition to or in place of the valve arrangement 400. More specifically, valve arrangement 500 is a torpedo valve that inserts into the inlet of many conventional humidifiers. Thus, like valve 400, valve 500 is easily retrofit in to an existing humidifier. Valve 500 includes a body 502 having a flow passageway orifice 504 defining therein. Compression springs 506 and 508 are positioned on a spring rod 510 and on opposite sides of the orifice 504. A sealing member 512 is positioned on a downstream side of orifice 504. Compression springs 506 and 508 contact sealing member 512. The spring constants (K) of the compression springs are different; however, compression spring 506 has a higher spring constant (K) than the spring constant (K) of compression spring 508. As a result, sealing member 512 is biased in a closed position adjacent to orifice 504.

In operation, valve 500 is oriented in the inlet of a humidifier such that pressurized gas from a pressure support device causes the sealing member 512 to move, thereby compressing spring 506 and expanding spring 508. As a result, flow passage orifice 504 opens and permits pressurized gas to pass through a humidifier inlet into the fluid holding chamber where the gas is humidified by the fluid contained in the humidifier. The humidified gas leaves the humidifier via an outlet. If fluid from the fluid holding chamber sloshes or is splashed toward valve arrangement 500 or if pressurized gas ceases to flow from the pressure support device (or is reduced below a predetermined threshold), then compression springs 506 and 508 cause the sealing member 512 to close flow passage orifice 506 (as shown in phantom) thereby preventing fluid from flowing upstream from the inlet passageway of the humidifier into the pressure support device.

Figure 23:
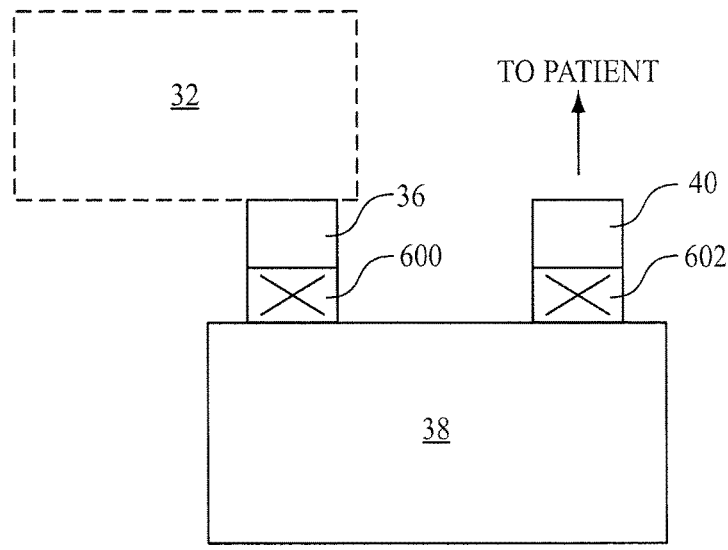
FIG. 23 is a schematic representation of a humidifier having a double valve configuration according to the principles of the present invention.

In the previous embodiments, a single valve, valve arrangement, or valve assembly is provided at the inlet of the humidifier to prevent or minimize back-splashing of fluid or the back-flow of gas or fluid from the inlet of the humidifier. The present invention also contemplates that any of the valve configurations contemplated by the present invention can also be provided at an outlet of the humidifier, with or without providing a valve at the inlet. FIG. 23 is a schematic representation of a humidifier 38 having a valve arrangement 600 positioned within inlet 36 and a valve arrangement 602 positioned in outlet 40. Essentially, valve arrangements 600 and 602 can be any one of the valve arrangements described herein.

In an exemplary embodiment, valve arrangement 600 is adapted so that the upstream pressure in inlet port is higher than the downstream pressure so as to maintain valve 600 in an open position. If the pressure drop across valve 600 falls below a threshold value, the valve moves to a closed position. On the other end, valve arrangement 602 is adapted so that when upstream pressure in outlet 40 is higher than the downstream pressure, valve 602 is maintained in an open position. If the pressure drop across valve 602 falls below a threshold value, valve 602 moves to a closed position. Closure of valves 600 and 602 also occurs if water is splashed toward valve 600 and/or valve 602.

Figure 24:
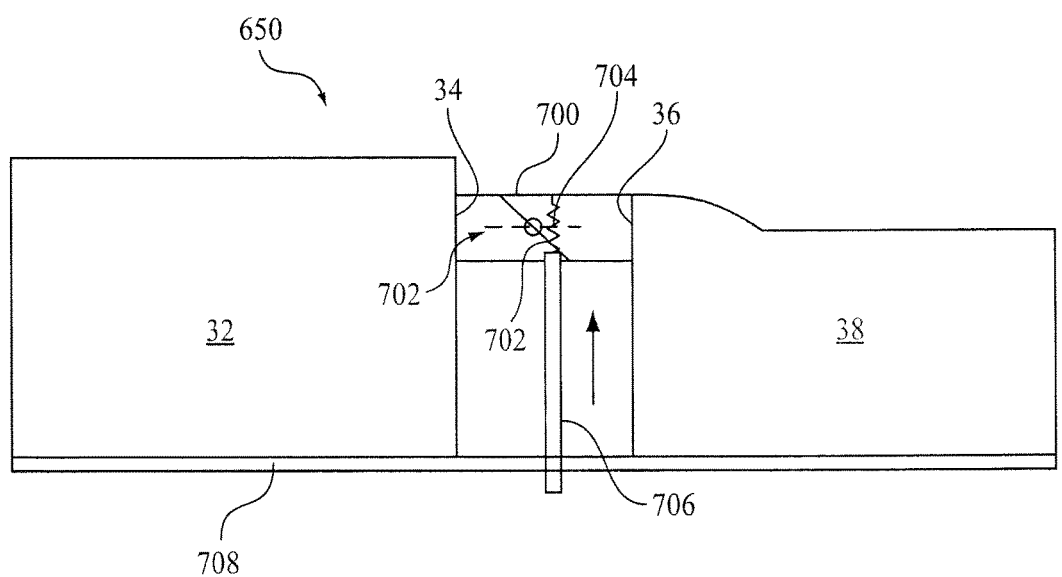
FIG. 24 is a schematic representation of a pressure support system having a ninth embodiment of a back-flow prevention valve according to the principles of the present invention.

FIG. 24 is a schematic representation of a pressure support system 650 that includes a ninth embodiment of a back-flow prevention valve 702 according to the principles of the present invention. Pressure support system 650 includes a pressure support device 32 fluidly coupled to a humidifier 38. More specifically, outlet 34 of the pressure support device is coupled to inlet 36 of humidifier 38 by a conduit 700. Conduit 700 includes a spring loaded valve 702 that is pivotally secured to conduit 700. Valve 702 is biased by a spring 704 in a closed position, so that the conduit is substantially blocked. A rod 706 passes through conduit 700 and contacts valve 702. Rod 706 also extends downwardly beyond a base portion 708 of pressure support system 650. When pressure support system 650 is resting on a flat surface, rod 706 is pushed in an upward direction so that valve 702 is moved by the rod in a horizontal or opened position (shown in phantom). When the device is either tipped over or lifted off of the flat surface, spring 704 forces valve 702 into a closed position preventing fluid from passing into the pressure support device 32. In other words, rod 706 contacting a surface causes valve 702 to be pushed into an open position. This embodiment is advantageous in that it blocks fluid from flowing back into the pressure support device whenever the system is lifted by a user or falls from the surface where it is sits. These events typically occur, for example, when a user carries the system to a source of water to fill the humidifier or if the system is accidentally pulled off of a night stand.

In the embodiment shown in FIG. 24, the automatic shutoff or kill-switch feature provided by the rod is shown as being provided in the conduit running between the pressure support device and the humidifier. It is to be understood that the present invention further contemplates providing this feature in the pressure support device itself, in the humidifier, or in both locations. It can be further appreciated that the valve and rod assembly shown in FIG. 24 is merely a simplistic representation of the mechanical components that provide the auto-enable/disable function. In actuality, a more complex system of levels, rods, switches, etc. may be provided to effect automatic shutoff or kill-switch feature.

Figure 25:
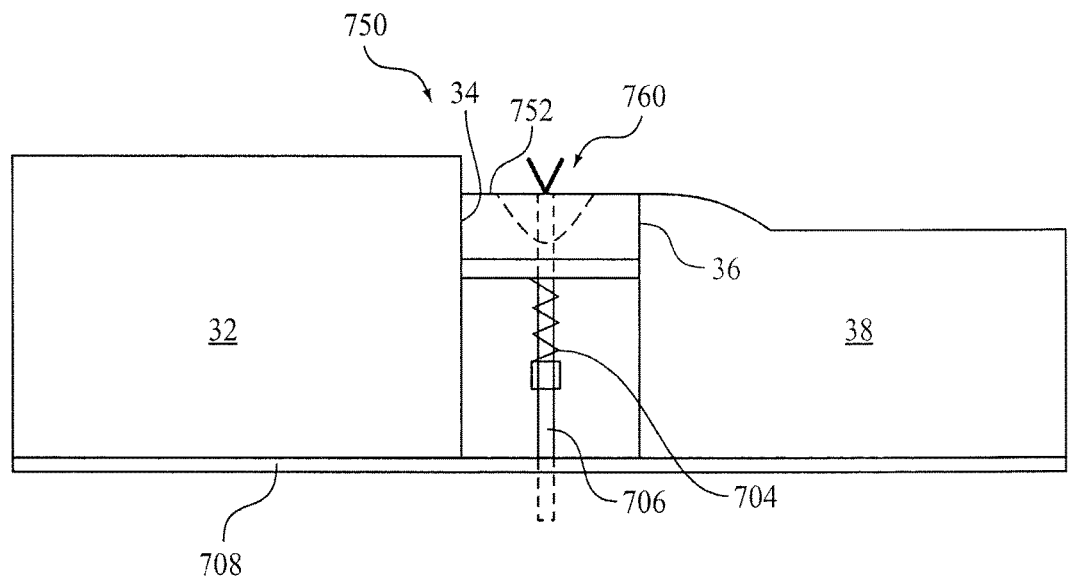
FIG. 25 is a schematic of a pressure support system having a tenth embodiment of a back-flow prevention valve according to the principles of the present invention.

For example, FIG. 25 discloses another embodiment of a pressure support system 750 similar to that shown in FIG. 24, except conduit 752 is a flexible tubing. A pinch valve 760 is positioned about the exterior of conduit 752. Rod 706 co-acts with pinch valve 760 so that when rod 706 rests against a flat surface, pinch valve 760 is in an open position and gas can pass from pressure support device 32 to humidifier 38. However, if pressure support system 750 is knocked over, lifted, or is otherwise removed from the flat surface, then rod 706 is biased downwardly (shown in phantom) by spring 704, and pinch valve 760 presses against flexible conduit 752, thereby preventing or substantially obstructing the fluid connection between the pressure support system and the humidifier.

The present invention further contemplates that an electronic valve, such as a solenoid valve, can replace any of the valves disclosed herein, such as valve 600, 602, 702 or 760. The valve can be electronically coupled to a kill switch, accelerometer, or any other sensing device so that the valve is actuated (opened or closed) based on an output of the sensing device. Hence, should the pressure support system be knocked or tipped over, accelerated or moved above a threshold value $a_1$, for a time greater than $t_1$, the solenoid valve will close. Closing the valve can be done directly, i.e., such as by actuating a valve based on the output of the sensor.

The present invention also contemplates controlling the operation of the pressure support system based on the output of a kill switch, accelerometer or other sensor, so that the pressure of the flow of gas provided to the valve is reduced or eliminated, thereby causing or allowing the valve to shut. In this manner, the valve is shut indirectly, i.e., by shutting the power off to the pressure support device, thereby causing the valve to close. In either scenario, a back-flow of fluid, gas, or both from the humidifier is prevented from reaching the pressure support device.

If an electronic valve is used, the present invention contemplates that the electrical conductors, connectors, or both can be imbedded in the humidifier body, for example by molding the conductors in the plastic chamber. Alternatively, or in addition, the conductors and/or connectors can be etched into the surface of the humidifier body. Imbedding or etching the connectors into the humidifier body is advantageous in that it minimizes the risk of the electrical conductors or connectors contacting the water contained in the humidifier body.

Figure 26:
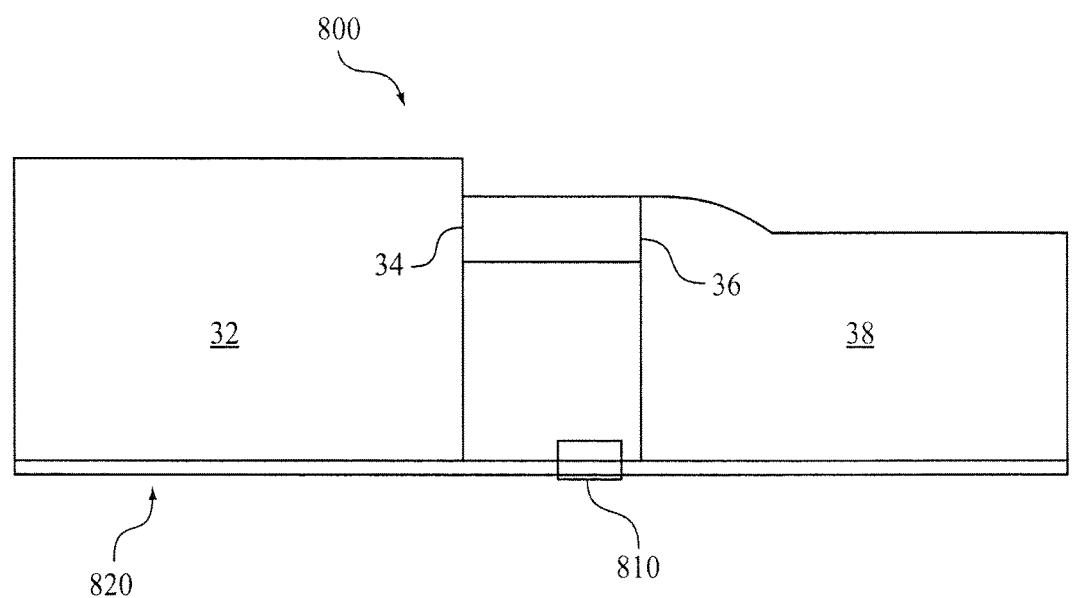
FIG. 26 is a schematic of a pressure support system having a kill switch.

FIG. 26 is a schematic of a pressure support system 800 having a kill switch 810 positioned proximate to a bottom surface 820 of the pressure support system. Of course, the kill switch can be located on the pressure support device, the humidifier, or at both locations. As long as kill switch 810 is resting on a flat surface, power is provided to pressure support device 32. However, once kill switch 810 is not resting on a surface, then power to the pressure support device is shut off. In this situation, the valve arrangement is biased in the closed position, preventing or reducing the flow of pressurized gas from pressure support device 32 into humidifier 38. As a result, a valve according to the embodiments discussed above, closes, thus preventing fluid, gas, or both, from flowing back into pressure support device 32 from the humidifier.

Kill switch 810 can be any device suitable to accomplish the function noted above. That is, the kill switch can be any device that detects when the pressure support device, humidifier, or both are properly situated on a surface or a level surface. Examples of devices that can detect whether the humidifier and/or pressure support device are situated on a surface include a pressure sensor, an optical monitor, a sonic transducer, and a proximity switch. Of course, multiple kill switches of like or dissimilar configurations can be used to achieve this purpose.

The present invention also contemplates monitoring various parameters of the pressure support system and causing a valve to block or unblock a gas flow path between the pressure support device and the humidifier based on or more of the monitored parameters. This is accomplished either be controlling the valve directly, if it is an electronic valve, or by controller the pressure generating device. The following is a list of exemplary parameters that can be monitored and used to control such a valve:

1) The operating temperature, pressure, humidity, or any other fluid related variable of the pressure support device, the humidifier, or both;

2) The special orientation of the pressure support device, the humidifier, or both (a tilt switch, kill switch);

3) The movement of the pressure support device, the humidifier, or both (an accelerometer);

4) The connection of any of the components in the pressure support system; and

5) The fluid level in the humidifier;

It is to be understood that this list is not intended to be a complete listing, but is provided to give examples of items that can be monitored and used as a basis for preventing fluid ingress into the outlet of the pressure support device from a humidifier.

Figure 27:
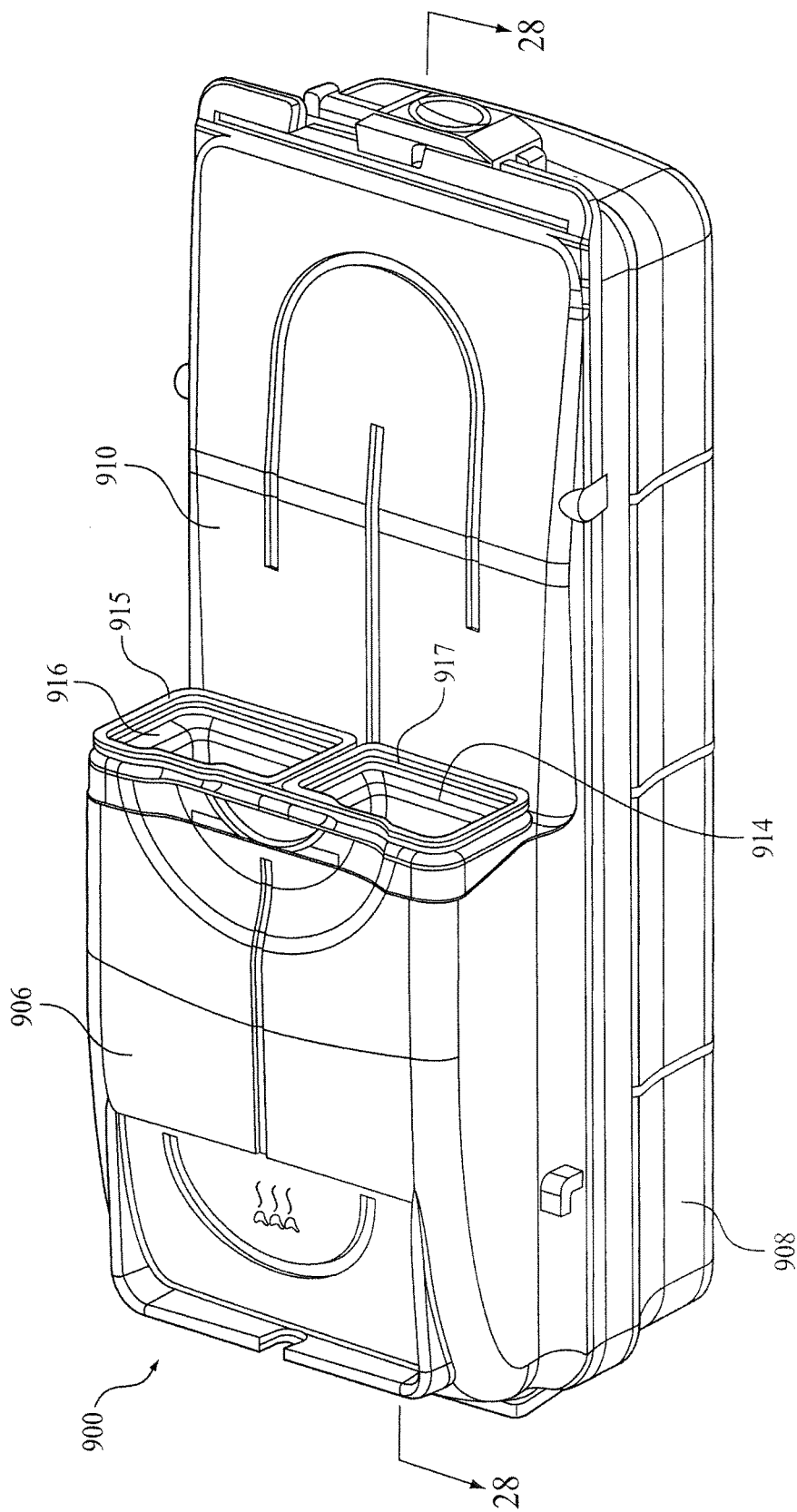
FIG. 27 is a perspective view of an eleventh embodiment of a humidifier having a back-flow prevention valve according to the principles of the present invention.
Figure 28:
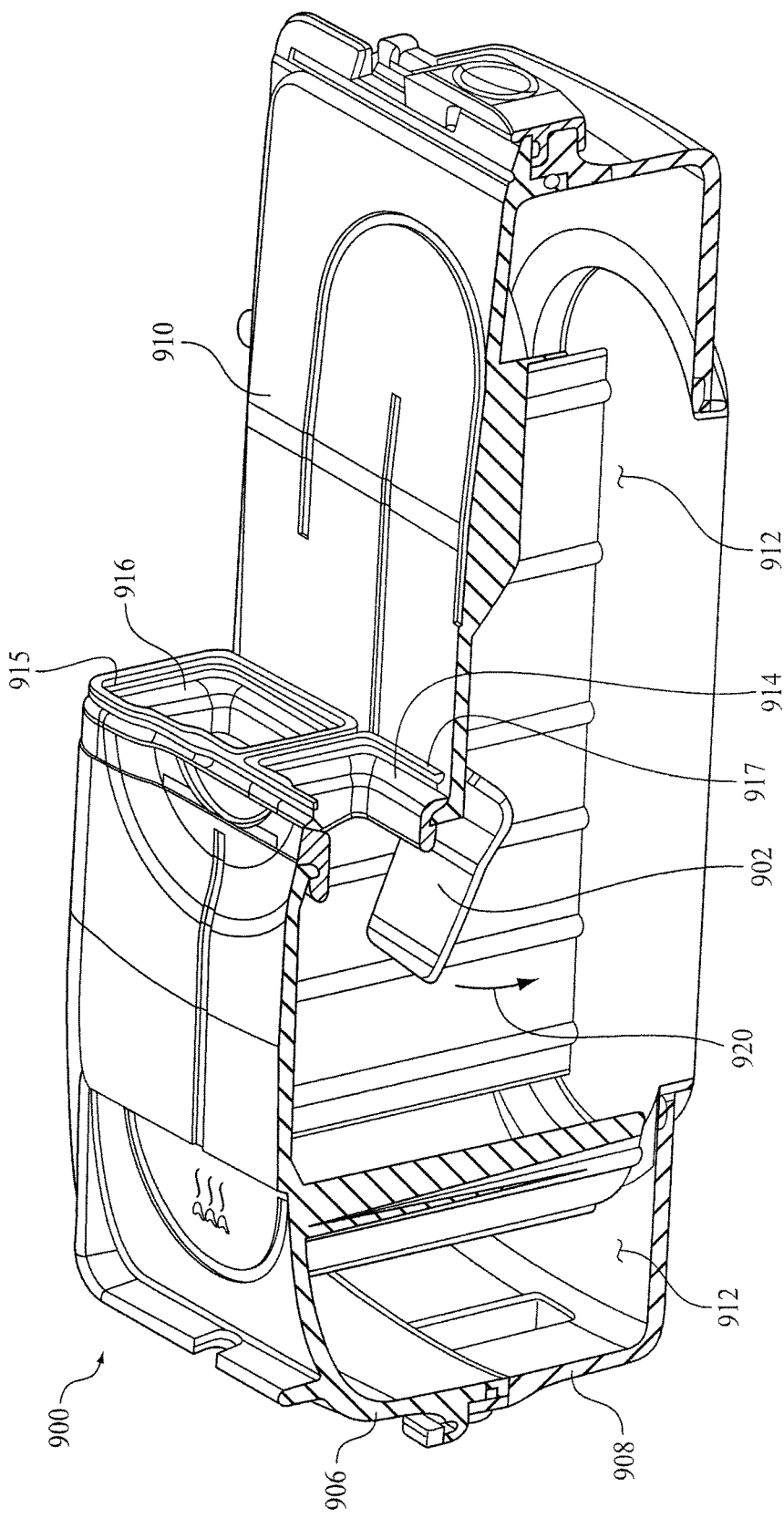
FIG. 28 is sectional view if the humidifier of FIG. 27 taken along line 28-28.

FIGS. 27 and 28 illustrate an eleventh embodiment of a humidifier 900 having a back-flow prevention valve 902 according to the principles of the present invention, and FIG.

Figure 29:
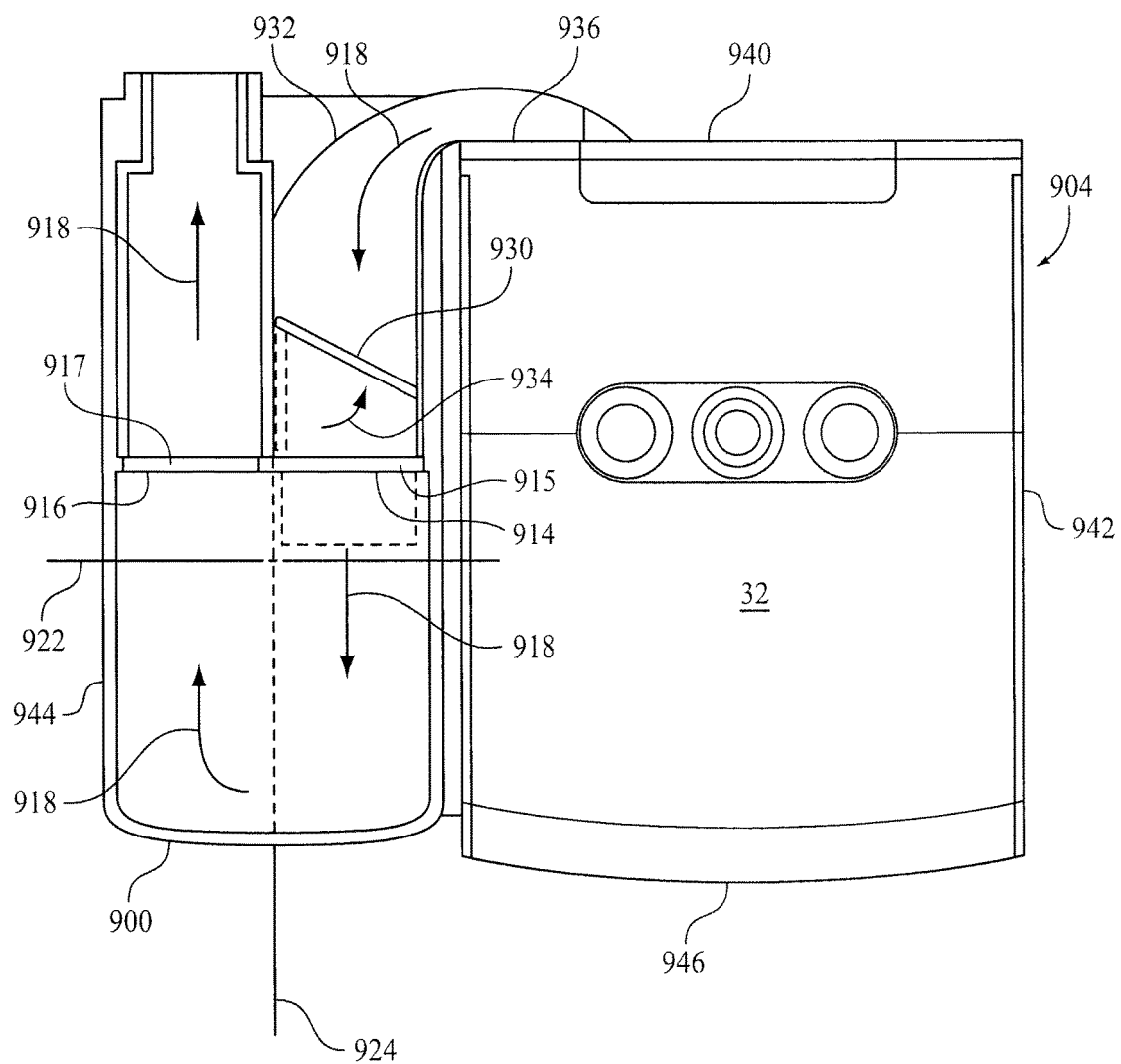
FIG. 29 is a schematic view of a pressure support system including a pressure support device coupled to the humidifier of FIG. 27.

29 illustrates the use of humidifier 900 in a pressure support system 904 that includes a pressure support device 32. Humidifier 900 is formed from an upper tray 906 and a lower tray 908 that assemble together to form a body 910 having a fluid holding chamber 912. An inlet 914 and an outlet 916 are formed side-by-side in upper tray 904. Gaskets 915 and 917 are provided on an external side of inlet 914 and outlet 916, respectively, to ensure a tight, gas-tight seal of the conduits to the inlet and outlet. As shown in FIG. 29, a flow of gas, as indicated by arrows 918, is provided by pressure support device 32 to inlet 914 of humidifier 900 where it is humidified and communicated to a patient circuit (not shown) via outlet 916.

As best shown in FIG. 28, back-flow prevention valve 902 is a flapper valve that is moveably coupled to upper tray 906. In an exemplary embodiment, flapper valve 902 is a relatively rigid member that is rotatably coupled to the upper member 906 so that the flapper valve rotates relative to the upper tray. Flapper valve 902 is sized and configured to block inlet 914 in a closed position and swings out of the way of the inlet in the open position. In this embodiment, valve 902 swings downward, as indicated by arrow 920 toward the fluid contained in the humidifier. The axis of rotation of the flapper valve is generally parallel to a lateral axis 922 of the humidifier. This configuration for the flapper valve provides the addition benefit that, even in the open position, the flapper valve helps prevent drops of fluid from splashing into inlet 914.

In operation, the flow of gas provided by the pressure support device to inlet 914 normally has a pressure that is sufficient to cause valve 902 to move to the open position and remain there. If fluid in the humidifier is tilted on a longitudinal axis 924, and if the fluid level is high enough, the fluid will contact the valve 902. The weight of the fluid will move the valve to the closed position. This embodiment of the present invention does not illustrate a biasing mechanism for maintaining the valve in a closed position. However, such a mechanism is contemplated by the present invention. For example, and without limitation, magnets and/or springs may be employed as a biasing mechanism. Biasing may also be accomplished by adapting valve 902 to be buoyant or weighted.

Pressure support system 904 includes a second back-flow prevention valve 930 that is operatively coupled to the inlet of the humidifier. In this exemplary embodiment, second back-flow prevention valve 930 is provided in a conduit 932 that couples the inlet of the humidifier to an outlet of pressure support device 32. Second back-flow prevention valve 930 is also a flapper valve that, when closed, substantially blocks conduit 932. Valve 930 is oriented such that the axis of rotation is generally perpendicular to lateral axis 922 and longitudinal axis 924. As a result, valve 930 moves from an open position (shown in phantom) to a closed position, as indicated by arrow 934.

During normal operation, the flow of gas provided by the pressure support device in conduit 932 has a pressure that is sufficient to cause valve 930 to move to the open position and remain there. However, when this flow is reduced or eliminated, flapper valve 930 is configured, arranged, and/or weighted or biased such that tilting the pressure support system so that the humidifier is above the pressure support device, e.g., rotating the system clockwise about axis 924, automatically causes the valve to shift from the open to the closed position. Thus, the actuation of valve 930 is dependent on the orientation of the pressure support system.

By providing a pair of back-flow prevention valves that are oriented in different planes, this embodiment of the present invention, minimizes the back-flow of fluid from the humidifier into the pressure support device regardless of the angle at which the pressure support system is tilted. For example, if the pressure support system is tilted onto side 940, back-flow prevention valve 902 is forced closed due to the weight of the fluid impacting that valve and/or the configuration of the valve, thereby preventing or minimizing the back-flow of fluid into conduit 932 and into pressure support device 32. If the pressure support system is tilted onto side 942, back-flow prevention valve 930 is moved to the closed position by the weight of the fluid impacting that valve and/or the configuration of the valve, again preventing or minimizing the back-flow of fluid into conduit 932 and into pressure support device 32. If the pressure support system is tilted onto side 944 or 946, there is no danger the fluid will flow back into the pressure support device as gravity will maintain the fluid away from an inlet 936 of the pressure support system.

Figure 30A:
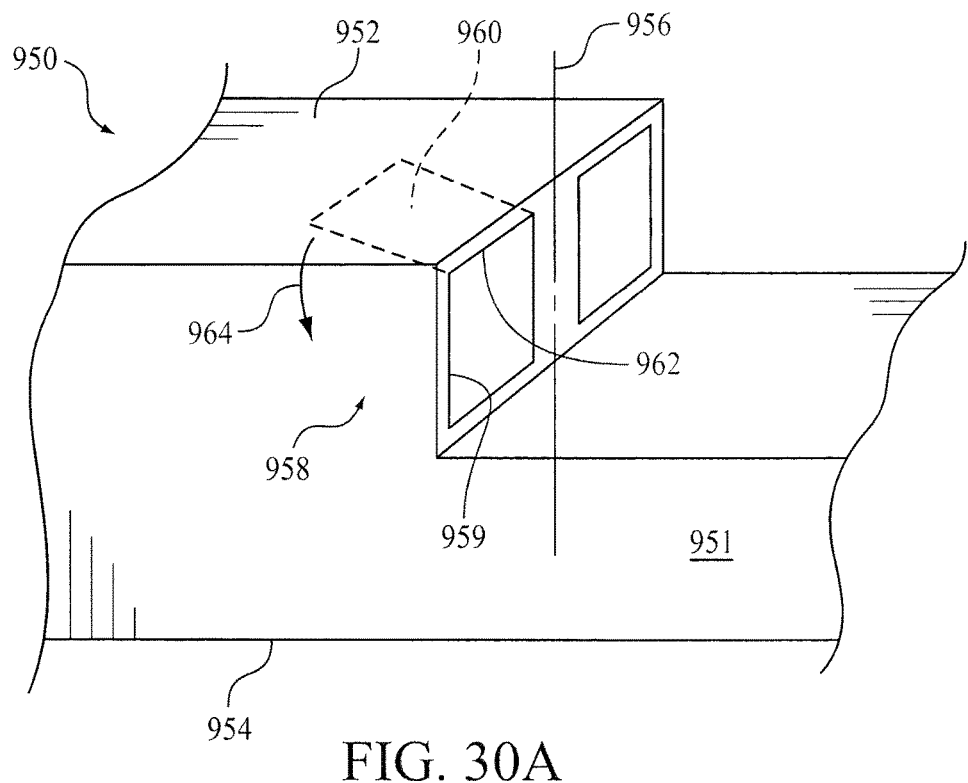
FIGS. 30A-30C illustrate alternative embodiments for the valve assembly showing the valve disposed in different orientations.
Figure 30B:
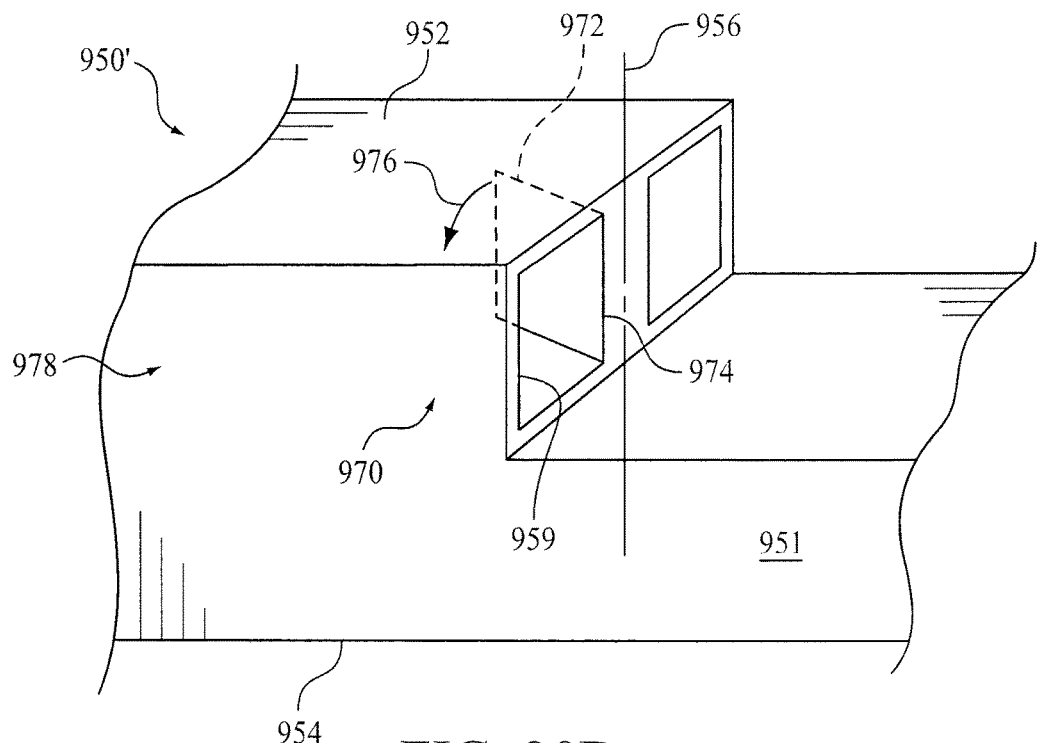
Figure 30C:
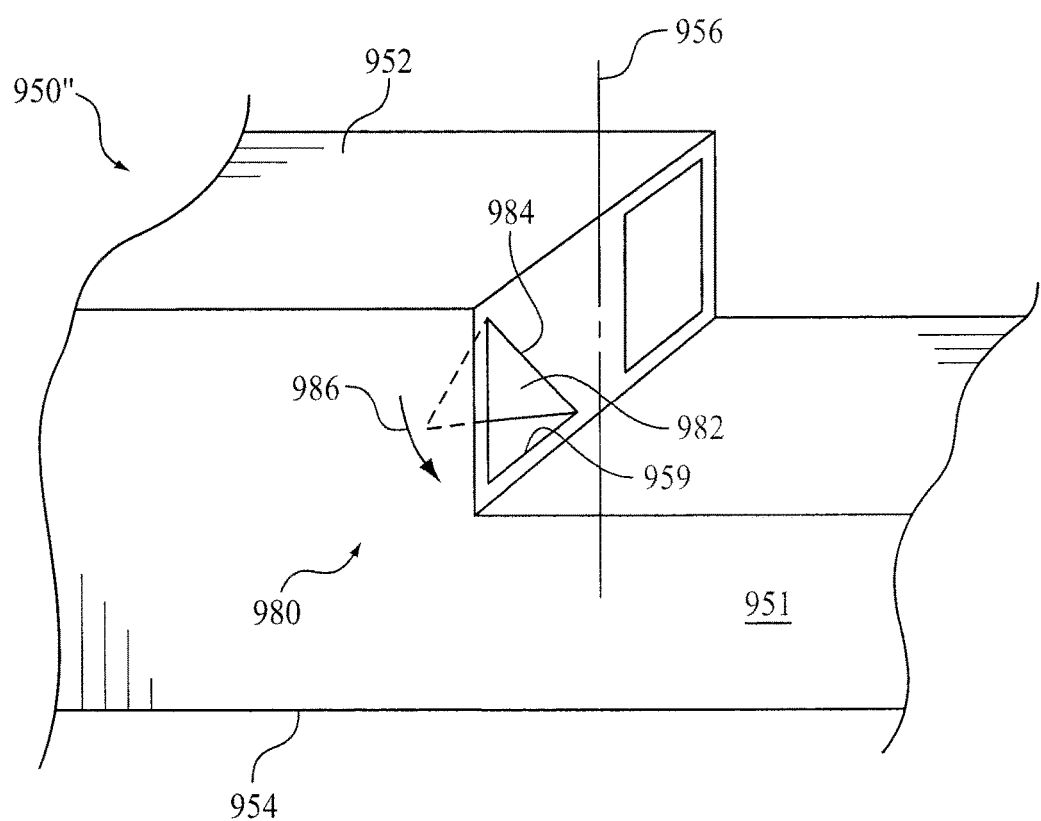

In the illustrated embodiment, valves 902 and 930 are coupled to the humidifier or the conduit via pins so that the flappers rotate on the pins. It is to be understood that other configurations for attaching the valves to the respective components of the pressure support system. For example, a living hinge can be used to join the flapper valve to the corresponding anchor points As alluded to above, the orientation of the moving element of the valve on the humidifier body can play a role in how and when the valve closes depending on the spatial orientation of the humidifier body. The present invention contemplates that the valve arrangement provided in the inlet passageway can be oriented however desired to achieve a certain valve closing characteristic. That is, the valve element can be oriented on the humidifier body so that it closes more easily if the humidifier body is tilted on its side, rather than on an end, or vice versa. FIGS. 30A-30C illustrate three alternative orientations for the valve element in a valve assembly to demonstrate this concept.

In FIG. 30A illustrates a humidifier 950 having a humidifier body 951 that, in normal operation, is oriented as shown, with a top portion 952 facing up and a bottom portion 954 facing down. Humidifier 950 includes a vertical axis 956. A valve arrangement 958 is provided in an inlet 959 of the humidifier body such that a valve 960 is oriented along an axis 962 that is generally perpendicular to vertical axis 956. In operation, when the flow of gas to the inlet falls below a threshold level, valve 960 closes, as indicated by arrow 964, thereby preventing a backflow of fluid out of the inlet. This arrangement is best suited for situation in which the a reduction or a cessation in the flow of gas to the inlet is intended to cause the inlet to be blocked, because in this embodiment, gravity will assist in urging valve 960 closed.

Humidifier 950' in FIG. 30B includes a valve arrangement 970 is provided in inlet 959 of the humidifier body such that a valve 972 is oriented along an axis 974 that is generally parallel to vertical axis 956. As a result of this orientation, valve 972 will tend to close, as indicated by arrow 976, thereby preventing a backflow of fluid out of the inlet, when the humidifier body is tilted on side 978, i.e., rotated counterclockwise relative to vertical axis 956. Of course, the present invention also contemplates locating valve 972 on the opposite side of the inlet so that the valve will close over the inlet when the humidifier body is rotated clockwise relative to vertical axis 956.

FIG. 30C illustrates still another configuration for a humidifier 950" having a valve arrangement 980 with a valve 982 that selectively closes inlet 959. Valve 982 is oriented on an axis 984 that is disposed at an angle relative to vertical axis 956 other than a zero or ninety degree angle. Valve 982 closes the inlet by moving as indicated by arrow 986. In short, FIGS. 30A-30C illustrate that the axis of rotation for the valve can be provided at an angle relative to vertical axis 956 ranging from 0° (FIG. to 30A) to 90° (FIG. 30B) or somewhere in between (FIG. 30C). The choice of this angle will determine the closing characteristics for the valve assembly with respect to the orientation of the humidifier body.

It can also be appreciated that the size, configuration, shape, weighting, and other features of the moveable valve element can be changed to achieve the desired closing characteristics. For example, the valve can be weighted so that it opens or closes in a more responsive fashion as the orientation of the humidifier body changes. Seals or gaskets can also be provided on the valve to control its sealing characteristics. In addition, the valve can be made from a rigid material, non-rigid material, or any combination thereof.

Figure 31A:
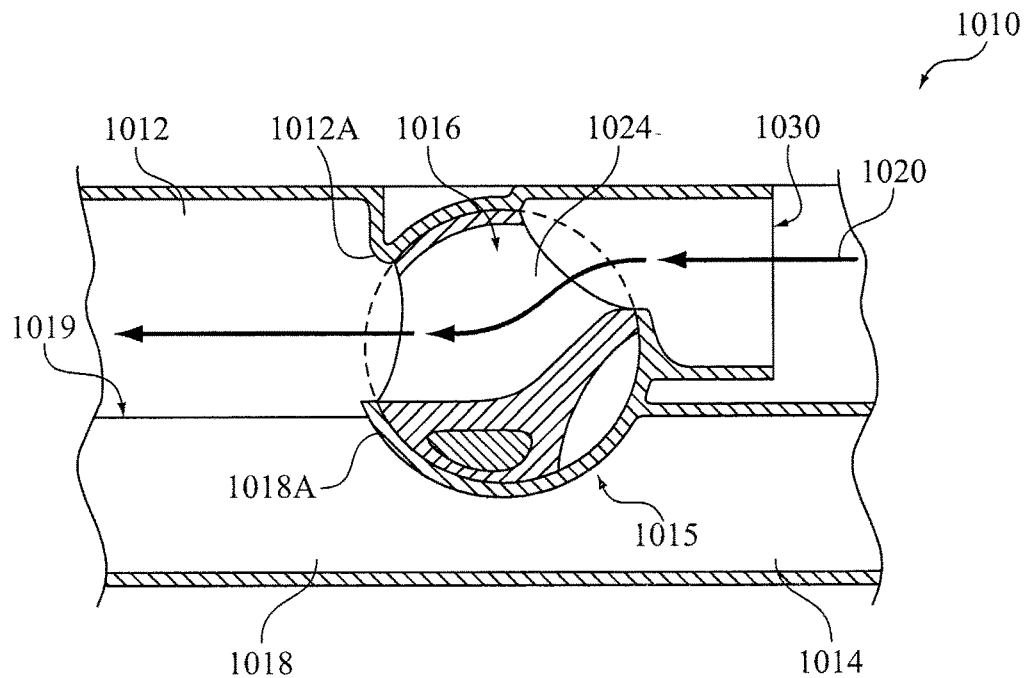
FIG. 31A is a side sectional view of a twelfth embodiment of a humidifier according to the principles of the present invention showing the valve in an open position.

FIG. 31A is a side sectional view of a portion of humidifier 1010 having a valve 1015 incorporated therein according to another embodiment. Valve 1015 generally includes valve seat and a valve plug 1016. Humidifier 1010 includes an upper cover 1012 and a lower cover 1018 which, when joined, are structured to form the valve seat. Specifically in the current embodiment, the valve seat is formed by upper cover portion 1012A and lower cover portion 1018A. In the current embodiment, the valve seat is generally located above the normal water level 1019 of fluid holding chamber 101.

Figure 31B:
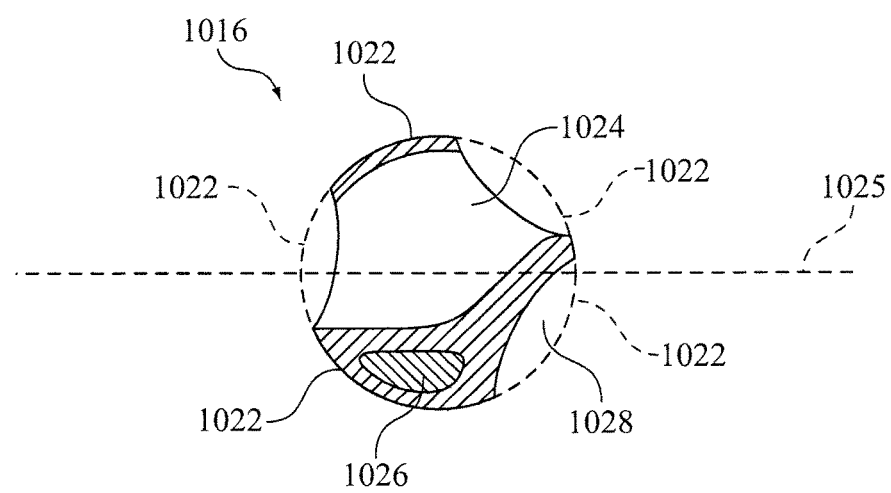
FIG. 31C is a side sectional view illustrating the humidifier of FIG. 31A in a tilted orientation showing the valve in a closed position.
FIG. 31D is a side sectional view illustrating the humidifier of FIG. 31A in a vertical orientation showing the valve in a closed position.
FIG. 31E is a side sectional view illustrating the humidifier of FIG. 31A in a inverted orientation showing the valve in a closed position.
Figure 31C:
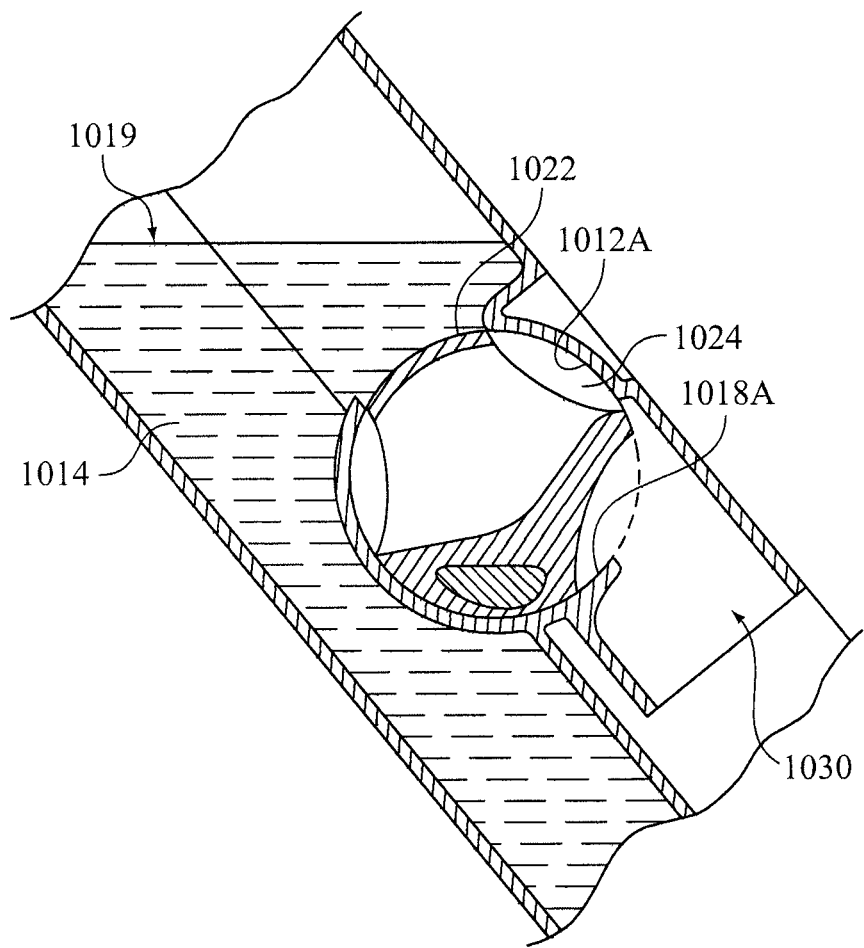
Figure 31D:
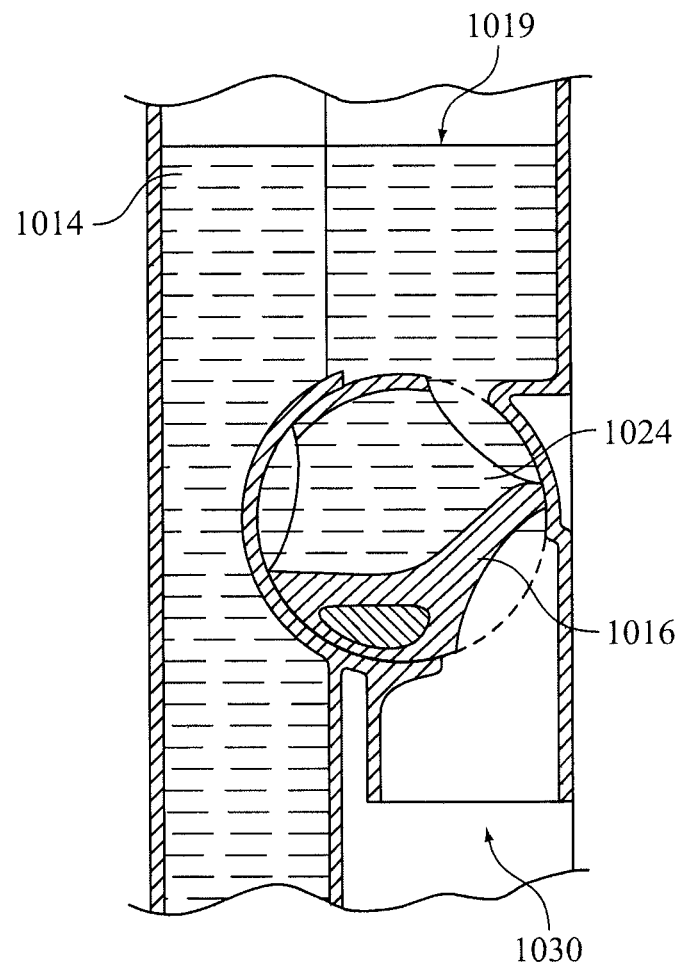
Figure 31E:
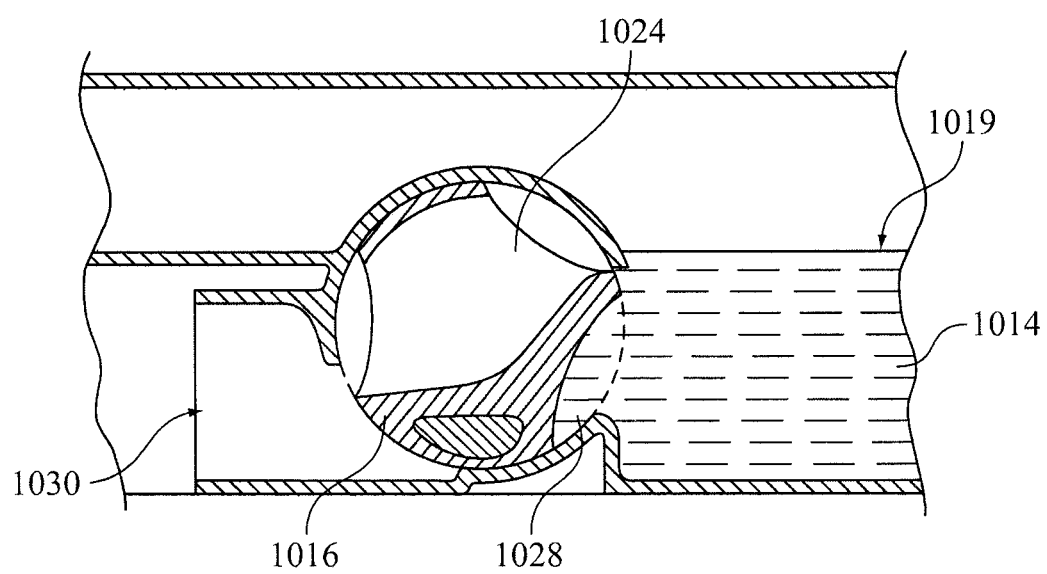

In the current embodiment, valve plug 1016 (shown in detail in FIG. 31B) includes an air channel 1024, a number of sealing surfaces 1022, a weighted portion 1026, and a number of cored areas 1028. Valve plug 1016 is adapted to cooperate with the valve seat such that, when in the open position (as shown in FIG. 31A) air is allowed to flow from inlet 1020 into fluid holding chamber 1014 and when in the closed position (as shown in FIGS. 31C-E) water and/or fluid laden vapor is prevented from flowing from the fluid holding chamber 1014 back into inlet 1030. Valve plug 1026 is adapted to freely rotate (in three dimensions) within the valve seat. When humidifier 1010 is properly oriented, weighted portion 1026 causes valve plug 1016 to substantially align relative to the valve seat such that a flow of air, as indicated by arrows 1020 in FIG. 31A, can pass from valve inlet 1030 to fluid holding chamber 1014. In the current embodiment, air channel 1024 includes a slight offset (shown relative to axis 1025, for example, FIG. 31B) which further prevents the back-flow of water from fluid holding chamber 1014 into inlet 1020 should the water level 1019 be higher than lower portion 1018A of the valve seat. Sealing surfaces 1022 are in contact with portion 1012A and portion 1018A of the valve seat to prevent the flow of air 1020 from circumventing air channel 1024 and/or to prevent a flow of water around valve plug 1016. Cored areas 1028 are adapted to reduce the weight of valve plug 1016 and/or enhance the responsiveness of weighted portion 1026.

FIGS. 31C-31E illustrate humidifier 1010 in tilted, vertical, and inverted orientations and show valve 1015 in a closed position. Referring to FIG. 31C, for example, when humidifier 1010 is in a tilted orientation, weighted portion 1026 causes valve plug 1016 to rotate relative to the valve seat until air channel 1024 is substantially blocked by upper portion 1012A and lower portion 1018A of the valve seat. Even thought water level 1019 is higher than valve 1015, sealing surface 1022 and upper portion 1012A and lower portion 1018A of the valve seat prevent water from flowing around valve plug 1016 into inlet 1030.

When humidifier 1010 is in a vertical orientation, weighted portion 1026 again causes valve plug 1016 to rotate relative to the valve seat. As can be seen in FIG. 31D, water may enter air channel 1024, however, air channel 1024 remains blocked from inlet 1030. Accordingly, water is prevented from back-flowing into inlet 1030. Likewise, when humidifier 1010 is in an inverted orientation, weighted portion 1026 again causes valve plug 1016 to rotate relative to the valve seat. As can be seen in FIG. 31E, water may enter into cored area 1028, however, air channel 1024 remains blocked from inlet 1030. Accordingly, water is prevented from back-flowing into inlet 1030.

Figure 32A:
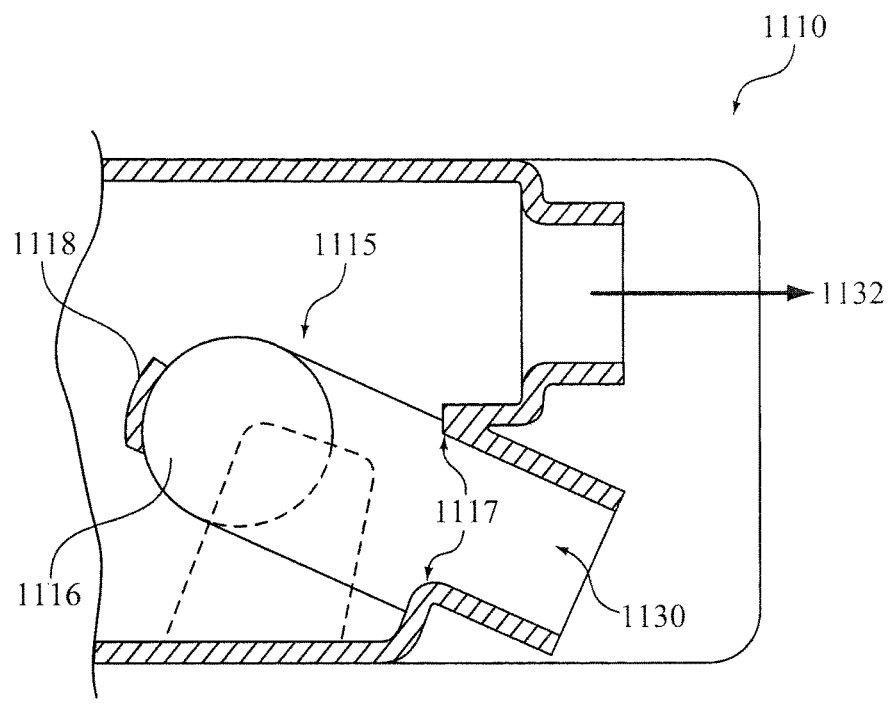
FIG. 32A is a top sectional view of a thirteenth embodiment of a humidifier according to the principles of the present invention showing the valve in an open position.
Figure 32B:
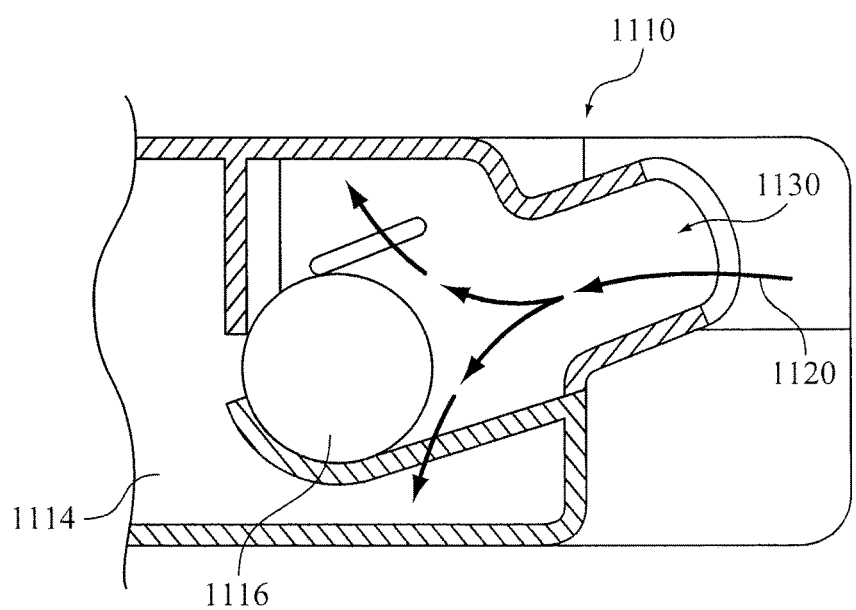
FIG. 32B is a side sectional view of the humidifier of FIG. 32A.

FIGS. 32A and 32B are top and side sectional views, respectively, of a portion of humidifier 1110 having a valve arrangement, generally indicated at 1115, according to yet another embodiment. This embodiment is generally similar to the previous embodiment shown in FIGS. 16-17 except that ball 1116, used to selectively block and unblock a valve seat 1117, is weighted and does not float. Support structure 1118 guides ball 1116 into valve seat 1117 in response to a change in the orientation of humidifier 1110. In an exemplary embodiment, support structure 1118 is configured such that gas and liquids flow freely in or around the support structure. For example, the support structure can be a cage or a bracket with a plurality of openings.

Figure 32C:
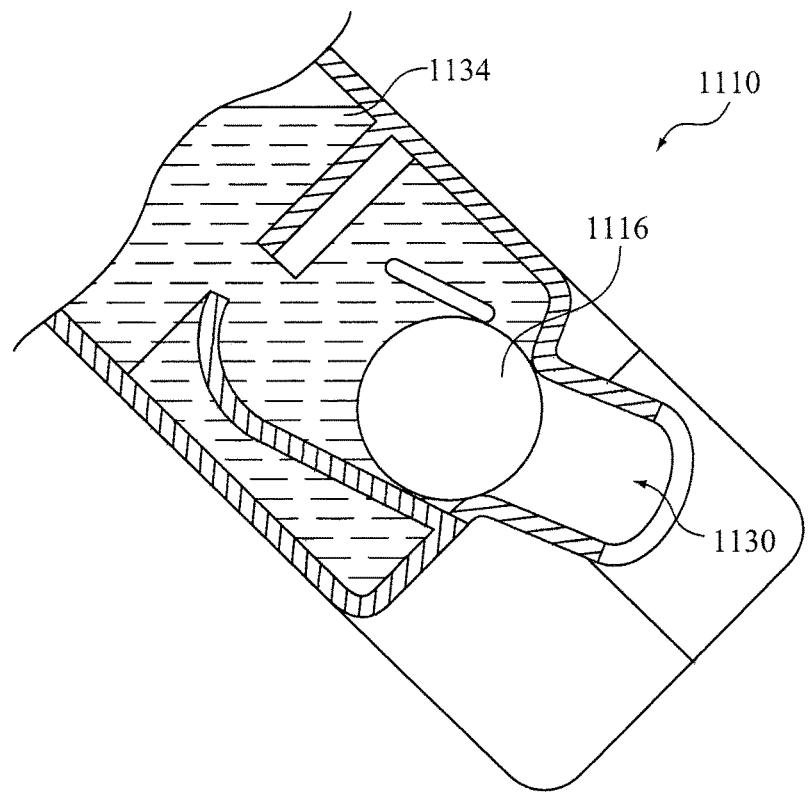
FIG. 32C is a side sectional view illustrating the humidifier of FIG. 32A in a tilted orientation showing the valve in a closed position.
Figure 32D:
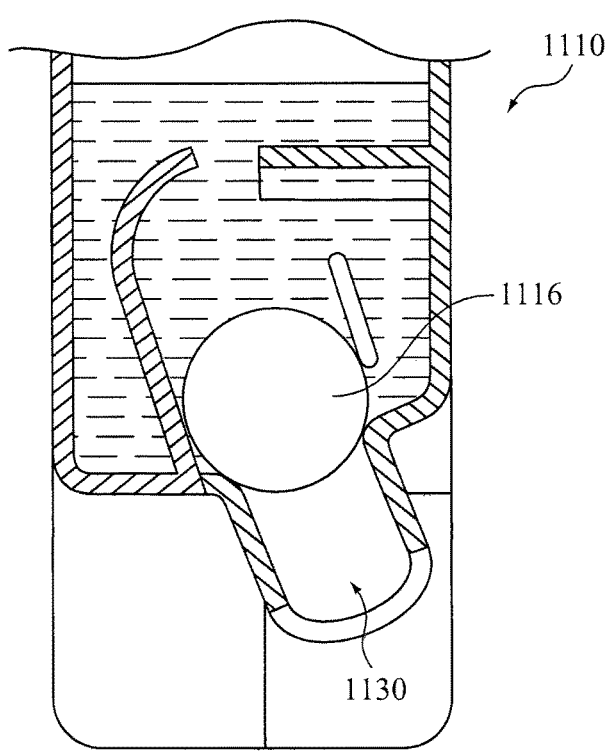
FIG. 32D is a side sectional view illustrating the humidifier of FIG. 32A in a vertical orientation showing the valve in a closed position.
Figure 32E:
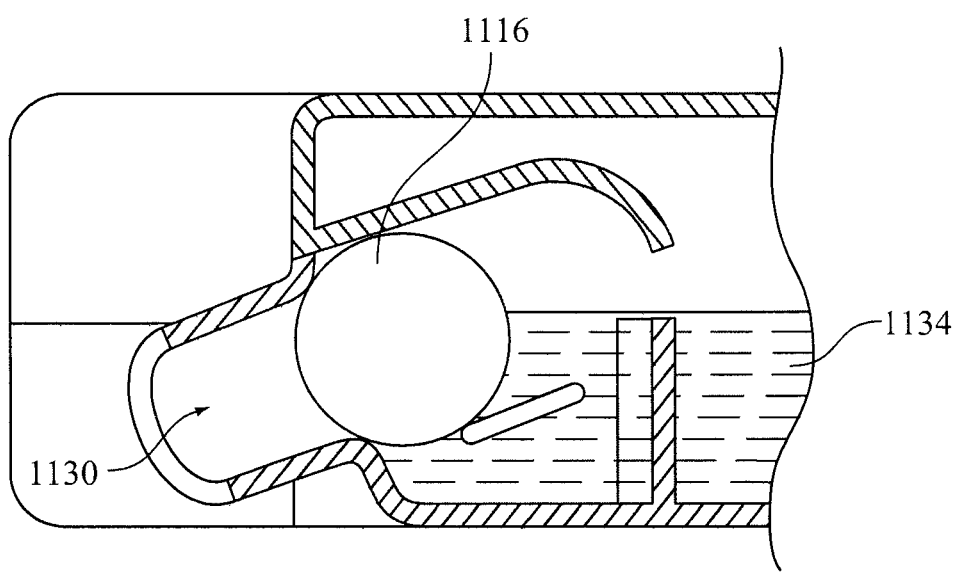
FIG. 32E is a side sectional view illustrating the humidifier of FIG. 32A in a inverted orientation showing the valve in a closed position.

During normal operation, as shown in FIGS. 32A-32B, the ball 1116 is spaced apart from valve seat 1117 and a substantially unobstructed gas flow path is provided at inlet 1130 of humidifier 1110 to fluid holding chamber 1114. Thus, gas flows relatively freely into fluid holding chamber 1114 as indicated by arrows 1120. As the humidifier is tilted (for example as shown in FIG. 32C) and/or turned (for example, turned vertically on end as shown in FIG. 32D), weighted ball 1116 pushes into seat 1117, thereby blocking the passageway inlet and preventing fluid and gas from flowing back out of inlet 1130. Humidifier 1110 does not include a biasing mechanism for urging the valve to an open position or closed position; however, it is contemplated that such a biasing mechanism may be added while remaining within the scope of the present invention. Although support structure 1118 is illustrated as being generally linear and stationary in design, it is contemplated that other designs may be employed. For example, and without limitation, a support structure having a slight curvature and which swivels about valve seat 1117 is contemplated.

Although the element that blocks the inlet is illustrated as being a ball, it can be appreciated that other configurations, geometrical shapes, and differently sized elements may be provided. Additionally, although not illustrated, it is contemplated that a biasing device, such as a magnet, spring, or other devices may be employed to bias the valve to the desired position.

It can be appreciated that the present invention utilizes at least one back-flow prevention valve to prevent back flow of fluid, such as water, from a humidifier into a pressure support device located upstream of the humidifier. Although the term "valve" is used herein to describe the backflow prevention device, it should be noted that this term is intended to cover any device, assembly, configuration, that is capable of moving between two positions: a first position in which fluid/gas is free to flow into and out of the inlet of the humidifier; and a second position in which fluid/gas is impeded, restricted, or blocked from flowing back through the inlet of the humidification system toward the pressure generator.

In an exemplary embodiment of the present invention, the back-flow prevention valve will only open if the pressure of the gas from a pressurized gas source, e.g., pressure support device 32, delivered to an inlet of the humidifier has a pressure Po that is greater than or equal to the biasing force acting on back-flow prevention valve. A flow of gas passes over fluid (water) contained within the fluid holding chamber and is humidified. The humidified gas passes through an outlet and is carried to the airway of a patient by a patient circuit and a patient interface. If the pressure of the gas (air) entering the humidifier is less than Po, the check valve will close, preventing fluid from splashing, sloshing, or otherwise flowing back into the outlet of the pressure support device from the inlet of the humidifier.

It is to be understood that the humidifier can have a variety of configurations. For example, the body portion can be rectangular, oval, frustro-conical, elliptical, etc. In addition, the humidifier can be combined with the pressure support device in a variety of combinations. For example, the humidifier may be rigidly connected to the pressure support device, separably connected, and/or connected via a length of patient circuit.

Therefore, as can be seen the present invention is an arrangement that prevents water from accidentally flowing from the humidifier 38 back to a CPAP unit 32 and the possibility of causing damage to the CPAP unit 32. Further, the present invention provides for a compact CPAP/humidifier apparatus 30.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

Figure 32F:
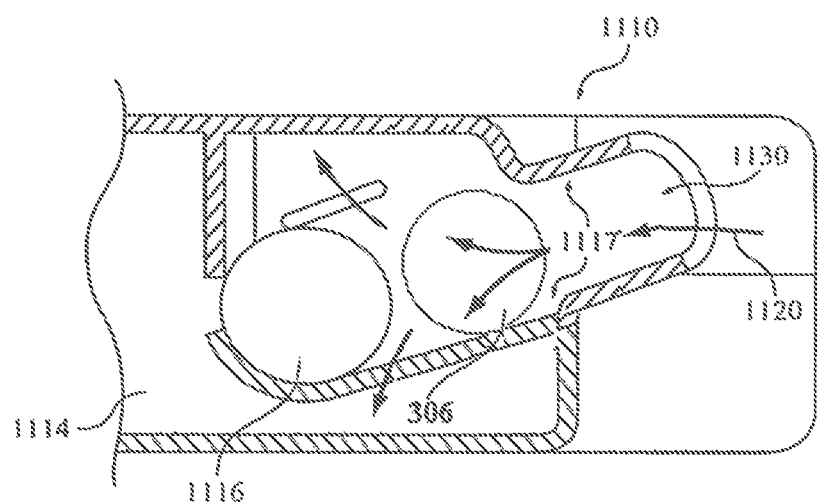
FIG. 32F is a side sectional view of the humidifier of FIG. 32A showing a buoyant ball placed between a weighted ball and a valve seat.

For instance, it is contemplated that the concepts of the embodiment illustrated in FIGS. 32A-32F may be combined with the concepts of the embodiment shown in FIGS. 16-17. A humidifier 1110' having a weighted ball 1116 and a buoyant ball 306, for example, is contemplated, as illustrated in FIG. 32F. In this embodiment, buoyant ball 306 is placed between weighted ball 1116 and valve seat 1117 within support structure 1118. Accordingly, should the water level within fluid holding chamber 1114 rise while humidifier 1110' is properly oriented, buoyant ball 306 will float and push into seat 1117, thereby blocking the passageway inlet and preventing fluid and gas from flowing back out of inlet 1130. Should humidifier 1110' be tilted, the responsiveness of valve 1115 is enhanced because weighted ball 1116 pushes buoyant ball 306 into seat 1117, thereby blocking the passageway inlet and preventing fluid and gas from flowing back out of inlet 1130.

What is claimed is:

1. A humidifier that humidifies a flow of pressurized gas provided to a patient comprising:
   a fluid holding chamber configured to hold fluid and conduct the flow of the pressurized gas through the fluid holding chamber from an inlet to an outlet of the humidifier; and
   a valve, the valve comprising:
      a valve seat; and
      a first ball housed in a support structure and normally resting on a sloped surface under the force of gravity, wherein the first ball is non-buoyant, wherein the sloped surface extends from the valve seat to an open position, and wherein the first ball rolls along the sloped surface within the support structure from the open position, in which the first ball is disengaged from the valve seat, to a closed position, in which the first ball is engaged with the valve seat, to seal the inlet of the humidifier upon tilting of the humidifier in a manner that would otherwise cause the fluid to back-flow out of the inlet,
   wherein the valve is operable to prevent the back-flow, in a direction opposite the flow of the pressurized gas.

2. The humidifier of claim 1, wherein the valve further comprises: a second ball housed in the support structure, wherein the second ball is moveable within the support structure.

3. The humidifier of claim 2, wherein the first ball is non-buoyant and the second ball is buoyant, and wherein the first ball engages with the valve seat in the closed position by pushing the second ball into the valve seat.

4. The humidifier of claim 1, wherein movement of the valve between the open position and the closed position is controlled based on an orientation of the humidifier.

5. The humidifier of claim 1, further comprising a second valve, wherein the second valve comprises a second valve seat and a second ball housed in a second support structure, wherein the second ball is moveable within the second support structure between a second open position in which the second ball is disengaged from the second valve seat and a second closed position in which the second ball is engaged with the second valve seat, wherein the second valve further comprises a biasing mechanism adapted to urge the valve to the closed position, and wherein the second valve is located within the inlet of the humidifier and the valve comprising the first ball is located within the outlet of the humidifier.

6. The humidifier of claim 1, wherein the first ball rolls within the support structure into engagement with the valve seat responsive to the humidifier being tilted.

7. The humidifier of claim 1, wherein the support structure further comprises a second sloped surface configured to guide the first ball back and forth between the valve seat and the open position, the second sloped surface being parallel to the first sloped surface and shorter than the first sloped surface.

8. A pressure support system comprising:
   a pressure support device adapted to generate a pressurized flow of gas;
   a humidifier that humidifies the pressurized flow of the gas provided to a patient having a body having an inlet, a fluid holding chamber, and an outlet, wherein the inlet is positioned upstream of and in fluid communication with the fluid holding chamber, and the outlet is positioned downstream of and in fluid communication with the fluid holding chamber; and
   a first valve positioned between an outlet of the pressure support device and the fluid holding chamber of the humidifier, wherein the first valve comprises a non-buoyant ball that normally rests on a sloped surface under the force of gravity and that rolls along the sloped surface from an open position, in which a gas flow path between the outlet of the pressure support device and the inlet of the humidifier is substantially unblocked, to a closed position, in which the ball engages a valve seat of the first valve such that the gas flow path is substantially blocked, to seal the inlet of the humidifier upon tilting of the pressure support system in a manner that would otherwise cause the fluid to back-flow out of the inlet, wherein the first valve is operable to prevent the back-flow, in a direction opposite the pressurized flow of the gas, and wherein the sloped surface extends from the valve seat to the open position.

9. The humidifier of claim 1, wherein the first ball engages with the valve seat when the humidifier is tilted less than ninety degrees, and wherein the first ball disengages with the valve seat when the humidifier is not tilted as such.

10. The pressure support system of claim 8, wherein the non-buoyant ball engages the valve seat when the pressure support system is tilted less than ninety degrees, and wherein the non-buoyant ball disengages the valve seat when the pressure support system is not tilted as such.

11. The pressure support system of claim 8, wherein the first valve further comprises a second sloped surface configured to guide the first ball back and forth between the valve seat and the open position, the second sloped surface being parallel to the first sloped surface and shorter than the first sloped surface.

\* \* \* \* \*